(12) United States Patent
Ehara et al.

(10) Patent No.: US 8,250,923 B2
(45) Date of Patent: Aug. 28, 2012

(54) ULTRASONIC INSPECTION METHOD AND ULTRASONIC INSPECTION APPARATUS

(75) Inventors: Kazuya Ehara, Hitachiohta (JP); Naoyuki Kono, Mito (JP); Masahiro Miki, Tokai (JP); Yoshio Nonaka, Hitachi (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 669 days.

(21) Appl. No.: 12/389,024

(22) Filed: Feb. 19, 2009

(65) Prior Publication Data

US 2009/0235749 A1 Sep. 24, 2009

(30) Foreign Application Priority Data

Mar. 19, 2008 (JP) ................................. 2008-070845

(51) Int. Cl.
*G01N 29/00* (2006.01)
*G01N 29/04* (2006.01)

(52) U.S. Cl. ............... 73/622; 73/598; 73/602; 376/252

(58) Field of Classification Search .................... 73/622, 73/596–598, 600, 602, 625–626; 376/252
See application file for complete search history.

(56) References Cited

U.S. PATENT DOCUMENTS

| | | | | |
|---|---|---|---|---|
| 4,270,389 A * | 6/1981 | Shiraiwa et al. | ................. | 73/612 |
| 4,305,297 A * | 12/1981 | Ries et al. | ........................ | 73/628 |
| 4,393,711 A * | 7/1983 | Lapides | .......................... | 73/592 |
| 4,522,064 A * | 6/1985 | McMillan | ........................ | 73/592 |
| 4,744,250 A * | 5/1988 | Ganglbauer et al. | ............. | 73/588 |
| 4,821,575 A * | 4/1989 | Fujikake et al. | ................. | 73/626 |
| 5,280,723 A * | 1/1994 | Aharoni et al. | .................. | 73/602 |
| 6,070,466 A * | 6/2000 | Taran et al. | ..................... | 73/622 |
| 6,497,150 B1 * | 12/2002 | Kruzic | ............................. | 73/611 |
| 7,168,322 B2 * | 1/2007 | Bardoux et al. | ................. | 73/588 |
| 7,412,890 B1 * | 8/2008 | Johnson et al. | .................. | 73/618 |
| 7,690,257 B2 * | 4/2010 | Meier et al. | ...................... | 73/588 |

(Continued)

FOREIGN PATENT DOCUMENTS

JP 60-8744 A 1/1985

(Continued)

OTHER PUBLICATIONS

Y. Nonaka et al., Development of Inspection Technology for Shroud Support of BWR, Jan. 2007, 8 pp., vol. 89, No. 02, Japan.

(Continued)

*Primary Examiner* — Helen C. Kwok
(74) *Attorney, Agent, or Firm* — Mattingly & Malur, P.C.

(57) ABSTRACT

An ultrasonic inspection method and ultrasonic inspection apparatus is capable of inspecting a weld line and of detecting a circumferential crack and an axial crack that are present in the weld line. An ultrasonic probe is placed on the surface of a structure and transmits an ultrasonic wave. The ultrasonic wave is transmitted at an angle in an X'-Z plane. The direction of a normal to the surface is defined as an X axis. The direction in which the weld line extends is defined as a Y axis. The direction perpendicular to the X axis and the Y axis is defined as a Z axis. An axis obtained by rotating the X axis around the Z axis is defined as an X' axis. A control mechanism performs signal processing of signals reflected from the defect or defects to detect the defect or defects and to measure the length of the defect or defects.

19 Claims, 31 Drawing Sheets

U.S. PATENT DOCUMENTS 7,693,251 B2 * 4/2010 Kono et al. .................. 376/252

FOREIGN PATENT DOCUMENTS

| | | |
|---|---|---|
| JP | 3-199961 A | 8/1991 |
| JP | 7-244033 | 9/1995 |
| JP | 11-183446 | 7/1999 |
| JP | 2005-195596 A | 7/2005 |
| JP | 2005-300224 | 10/2005 |
| JP | 2007-309771 A | 11/2007 |

OTHER PUBLICATIONS

"Automated UT Examination of BWR H8 & H9 Core Shroud Welds Using Phased Array Techniques" by H. Diaz, et al.

* cited by examiner

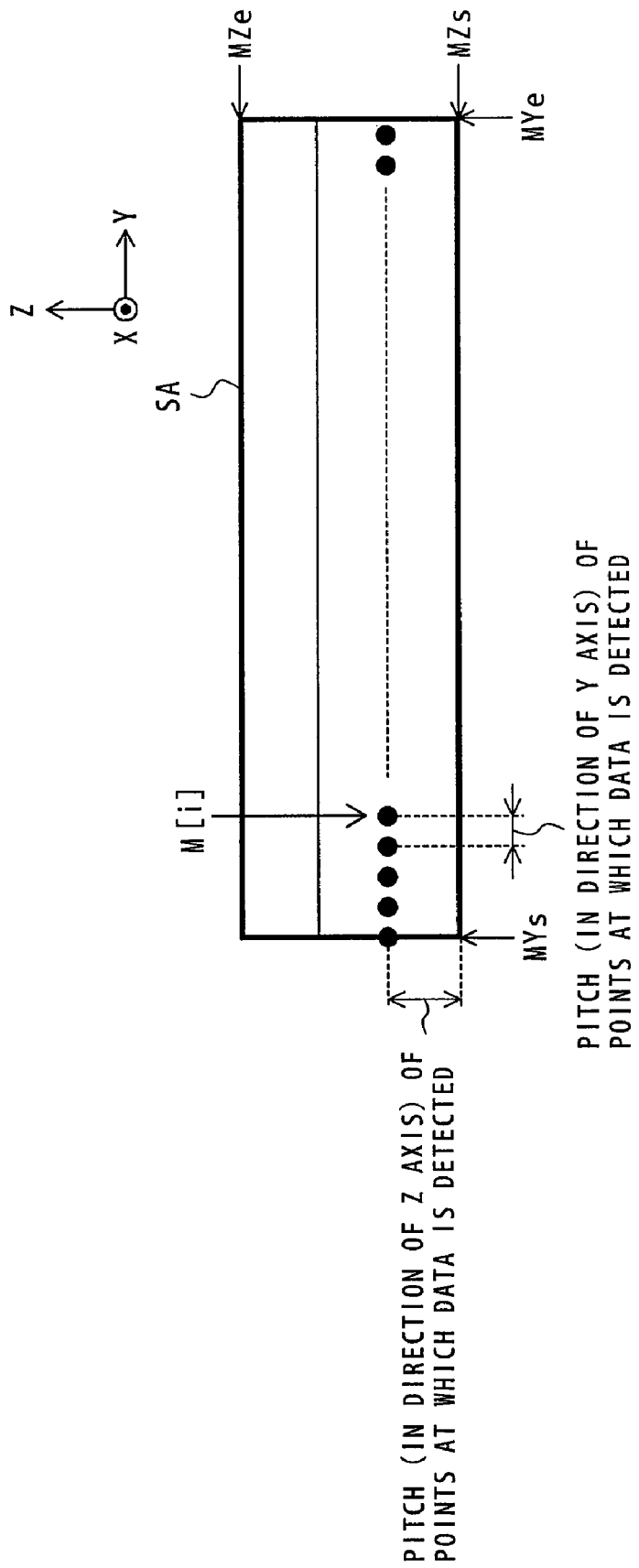

ULTRASONIC INSPECTION METHOD AND ULTRASONIC INSPECTION APPARATUS

BACKGROUND OF THE INVENTION

1. Field of the Invention

The present invention relates to an ultrasonic inspection method and to an ultrasonic inspection apparatus for inspecting metal or the like. The invention more particularly relates to an ultrasonic inspection method and to an ultrasonic inspection apparatus for inspecting a welded part for joining a structure (tube or vessel) partially or entirely having a cylindrical shape and another structure along a circumferential direction or along an axial direction or a direction in which a weld line extends with respect to the structure having the cylindrical shape.

2. Description of the Related Art

A method, such as an ultrasonic inspection method for inspection using an ultrasonic wave has been generally used as a nondestructive inspection method for inspecting a solid object such as metal. The following three inspection methods are known as ultrasonic inspection methods for inspecting a welded part (provided in a reactor pressure vessel) for joining a structure (tube or vessel) partially or entirely having a cylindrical shape and another structure along a circumferential direction or axial direction (direction of a welding line) of the structure having the cylindrical shape.

As the first method, an ultrasonic probe is placed on an inner surface of a penetration (a stub weld of a control rod drive mechanism attached to a lower head of a reactor pressure vessel) of the reactor pressure vessel to inspect the penetration through an immersion method in which water is injected in the penetration (refer to, for example, JP-A-7-244033).

As the second method, an ultrasonic probe is placed in a penetration (a stub weld of a control rod drive mechanism) of the bottom of a reactor pressure vessel, i.e., is placed on the inner side of the reactor pressure vessel to inspect the penetration (stub weld) (refer to, for example, JP-A-2005-300224).

As the third method, an ultrasonic probe is placed on the outer side of a reactor pressure vessel to inspect a welded part for joining the reactor pressure vessel and a structure provided in the reactor pressure vessel (refer to, for example, Non-Patent Document 1: AUTOMATED UT EXAMINATION OF BWR H8 & H9 CORE SHROUD WELDS USING PHASED ARRAY TECHNIQUES (Hector Diaz, Steven J. Todd, IHI Southwest Technologies, Inc.).

SUMMARY OF THE INVENTION

In the conventional inspection methods, however, the ultrasonic probe is placed in the structure in order to inspect a portion of a weld, from the side of the welded part. An ultrasonic probe cannot directly approach and inspect the welded part depending on the place or work environments in some cases. In this case, a large-scale scanning apparatus is required to scan a portion using the ultrasonic probe, and it is not easy to inspect the portion.

In addition, the surface of the welded part is not simple or is mechanically processed using a grinder in many cases. An irregular shape such as roughness or undulation may be present on the surface of an inspection target. When the inspection target is inspected from the inside of the structure (or from the side of the weld line) by using an ultrasonic wave, the efficiency of incidence of the ultrasonic wave on the inspection target may not be constantly maintained, and a signal received from the inspected portion may vary. This results in difficulty in evaluation of a defect.

Furthermore, Non-Patent Document 1 only discloses detection and sizing of a circumferential crack (defect extending in a direction parallel to a direction in which the weld line extends) during an inspection from the outer side of the pressure vessel. Non-Patent Document 1 does not disclose detection and sizing of an axial crack (defect extending in a direction perpendicular to the direction in which the weld line extends).

An object of the present invention is to provide an ultrasonic inspection method and ultrasonic inspection apparatus capable of easily performing an inspection and detecting a circumferential crack and an axial crack that are present in a weld line.

(1) To accomplish the object, the ultrasonic inspection method according to the present invention comprises the steps of: placing an ultrasonic probe on a first surface of a first structure that is a tube or a vessel, which partially or entirely has a cylindrical shape, the first surface of the first structure being located on the opposite side to a second surface of the first structure on which a welded part is present, the welded part joining the first structure and a second structure along a circumferential direction or axial direction of the first structure having the cylindrical structure; transmitting an ultrasonic wave from the ultrasonic probe at an optional angle in an X'-Z plane defined by an X' axis and a Z axis, when the direction of a normal to the first surface of the first structure is defined as an X axis, a direction in which the welded part extends is defined as a Y axis, a direction perpendicular to the X axis and the Y axis is defined as a Z axis, and an axis obtained by rotating the X axis around the Z axis is defined as an X' axis; and receiving a signal reflected from a defect present in the welded part to detect the defect.

The ultrasonic inspection method according to the present invention makes it possible to easily inspect the welded part and detect a circumferential crack and an axial crack that are present in the welded part.

(2) In the method described in item (1), preferably, when the ultrasonic probe moves in the Y axis or the Z axis and transmits the ultrasonic wave at an optional angle in the X'-Z plane to inspect the welded part, the result of the inspection (B scan) is displayed; a target area is specified from the inspection result, and an accumulated value of the intensity of an echo generated in the specified target area or a variation of the intensity of the echo is obtained; and the accumulated value or variation obtained at a data acquisition point is compared with the accumulated value or variation obtained at another data acquisition point to detect a defect.

(3) In the method described in item (1), preferably, when the ultrasonic wave is transmitted at the optional angle to scan the welded part, the length of the defect is measured based on the signal reflected from the defect.

(4) In the method described in item (1), preferably, data on an area in which an echo spreads and a cross-sectional drawing showing the welded part to be inspected are overlapped or overlaid based on the position of a reflection source and the resulting image is displayed, the position of the reflection source being calculated based on a beam path distance of an echo caused by the shape of the first structure and on an incident angle of the ultrasonic wave on the first surface of the first structure with respect to a normal to the first surface of the first structure.

(5) To accomplish the object, the ultrasonic inspection apparatus according to the present invention comprises: an ultrasonic probe for transmitting an ultrasonic wave and receiving a signal reflected from a defect present in a welded part, the ultrasonic probe being placed on a first surface of a first structure that is a tube or a vessel, which partially or entirely has a cylindrical shape, the first surface of the first structure being located on the opposite side to a second surface of the first structure on which a welded part is present, the welded part joining the first structure and a second structure along a circumferential direction or axial direction of the first structure having the cylindrical structure; control means for controlling the ultrasonic wave transmitted by the ultrasonic probe to cause the ultrasonic wave to be transmitted at an optional angle; ultrasonic wave direction changing means for changing the direction of the transmission of the ultrasonic wave from the direction of an X axis to the direction of an X' axis to ensure that the ultrasonic wave is transmitted in the first structure from the ultrasonic probe in an X'-Z plane defined by the X' axis and a Z axis, when the direction of a normal to the first surface of the first structure is defined as the X axis, a direction in which the welded part extends is defined as a Y axis, a direction perpendicular to the X axis and the Y axis is defined as the Z axis, and an axis obtained by rotating the X axis around the Z axis is defined as the X' axis; and position changing means for moving the ultrasonic probe in the direction in which the welded part extends or in a direction perpendicular to the direction in which the welded part extends, wherein the defect present in the welded part is detected based on the signal reflected from the defect present in the welded part.

The ultrasonic inspection apparatus according to the present invention is capable of easily inspecting the welded part and detecting a circumferential crack and an axial crack that are present in the welded part.

(6) In the ultrasonic inspection apparatus described in item (5), preferably, the ultrasonic wave direction changing means is provided between the first surface of the first structure and the ultrasonic probe and is made of a medium in which the ultrasonic wave propagates at a speed different from that at which the ultrasonic wave propagates in the first structure.

(7) In the ultrasonic inspection apparatus described in item (5), preferably, when the ultrasonic probe moves in the Y axis or the Z axis and transmits the ultrasonic wave at an optional angle in the X'-Z plane to inspect the welded part, the control means displays the result of the inspection, specifies a target area from the inspection result, obtains an accumulated value of the intensity of an echo generated in the target area or a variation of the intensity of the echo, and compares the accumulated value or variation obtained at a data acquisition point with the accumulated value or variation obtained at another data acquisition point to detect a defect.

(8) In the ultrasonic inspection apparatus described in item (5), preferably, data on an area in which an echo spreads and a cross-sectional drawing showing the welded part to be inspected are overlapped, or overlaid, based on the position of a reflection source, and the resulting image is displayed, the position of the reflection source being calculated based on a beam path distance of an echo caused by the shape of the first structure and on an incident angle of the ultrasonic wave on the first surface of the first structure with respect to a normal to the first surface of the first structure.

According to the present invention, it is possible to easily inspect a welded part, detect a circumferential crack and an axial crack that are present in the welded part, and reduce the time for the inspection.

BRIEF DESCRIPTION OF THE DRAWINGS

FIGS. 13A to 13C are explanatory diagrams showing the method for performing the inspection by means of the ultrasonic inspection apparatus according to the embodiment of the present invention.

DESCRIPTION OF THE PREFERRED EMBODIMENTS

The configuration and operations of an ultrasonic inspection apparatus according to a first preferred embodiment of the present invention are described below with reference to FIGS. 1 to 27B. In the present embodiment, a reactor pressure vessel of a boiling water reactor (BWR) is used as a first structure having a cylindrical shape; an in-reactor structure such as a shroud support and a plate is used as a second structure; and a welded part for joining the first structure and the second structure is used as a welded part, as an example.

The state in which the ultrasonic inspection apparatus according to the present embodiment is installed is first described with reference to FIGS. 1 and 2.

Figure 1:
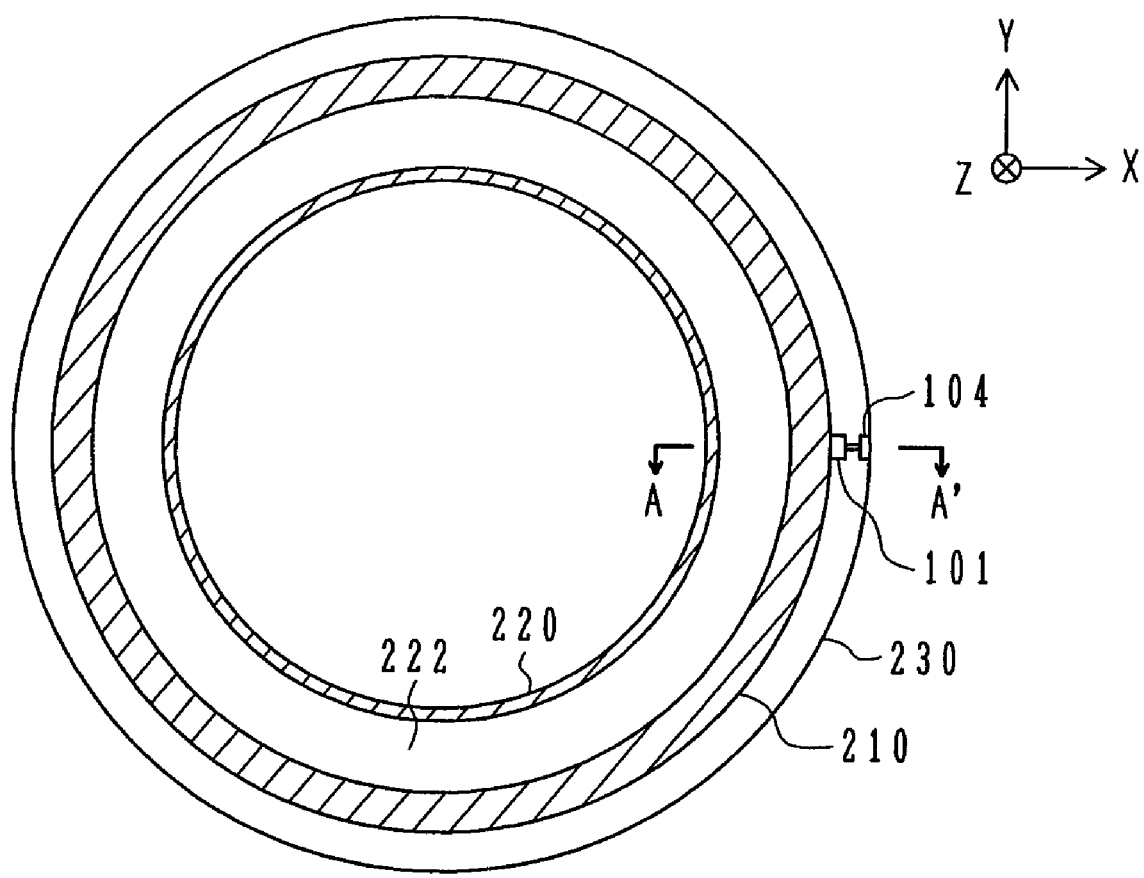
FIG. 1 is a plan view of an ultrasonic inspection apparatus according to an embodiment of the present invention and shows the state in which the ultrasonic inspection apparatus is installed.

FIG. 1 is a plan view of the ultrasonic inspection apparatus according to the present embodiment and shows the state in which the ultrasonic inspection apparatus is installed. FIG. 2 is an enlarged cross-sectional view taken along line A-A' of FIG. 1. In FIGS. 1 and 2, the same reference numerals denote the same parts. An axial direction of a pressure vessel 210 is defined as the direction of a Z axis. A radial direction of the pressure vessel 210 is defined as the direction of an X axis. A tangential direction perpendicular to the radius direction is defined as the direction of a Y axis.

Figure 2:
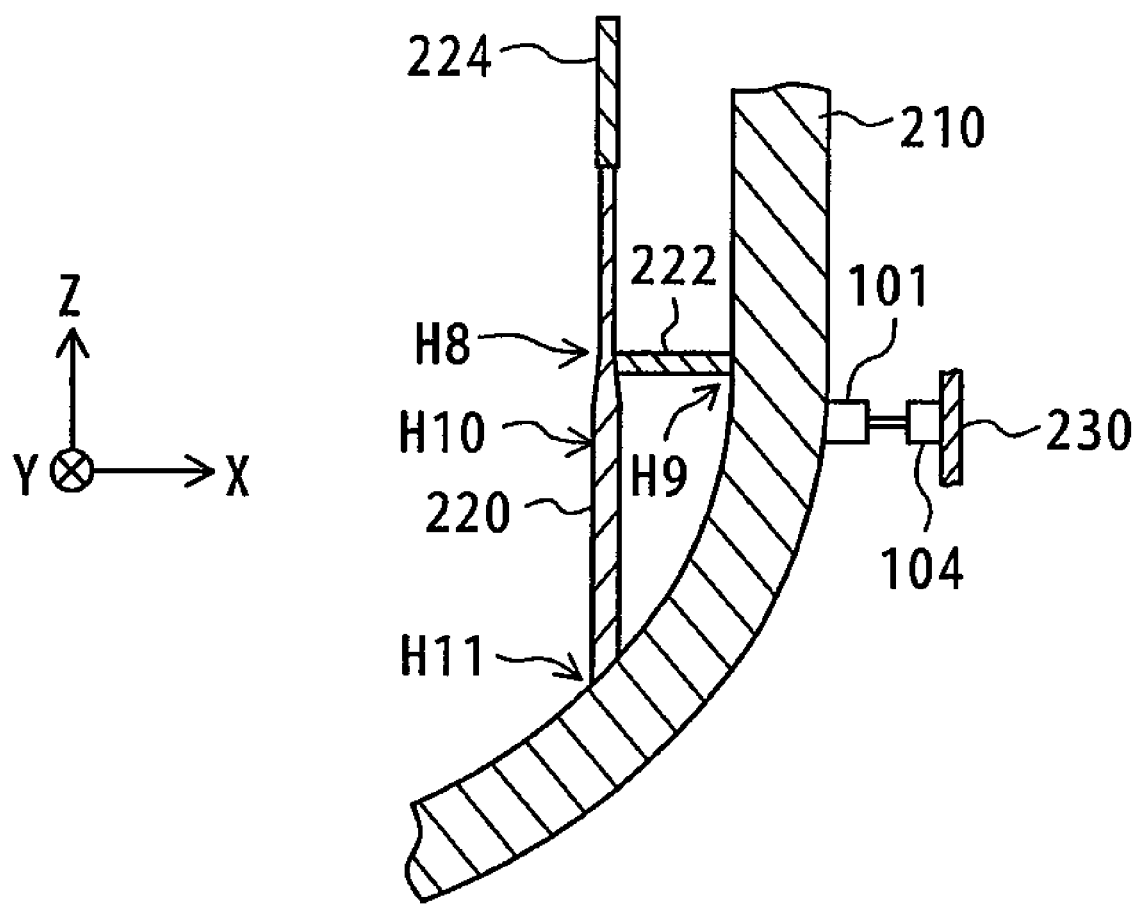
FIG. 2 is a cross-sectional view taken along line A-A' of FIG. 1.

As shown in FIGS. 1 and 2, the in-reactor structure including a shroud support 220 and a plate 222 is arranged in the pressure vessel 210 of the boiling water reactor (BWR). The pressure vessel 210 is made of carbon steel, for example. The thickness of the pressure vessel 210 is 160 mm, for example. The shroud support 220 and the plate 222 hold a shroud 224. The shroud support 220 has a cylindrical shape above an H10 weld line. In addition, the shroud support 220 has a rectangular plate shape under the H10 weld line. The plate 222 has a ring shape. The shroud support 220 and the plate 222 are made of a material such as INCONEL®.

An outer circumferential side portion of the plate 222 is welded to an inner surface of the pressure vessel 210 at an H9 part indicated by an arrow shown in FIG. 2. This welded part is called an H9 weld line. A lower edge portion of the shroud support 220 is welded to the inner surface of the pressure vessel 210 (specifically, to the inner surface of a lower head of the pressure vessel) at H11 parts indicated by an arrow shown in FIG. 2 at a constant interval in a circumferential direction of the pressure vessel 210. Each of these welded parts is called an H11 weld line. An inner circumferential side portion of the plate 222 is welded to an outer surface of the shroud support 220 at an H8 part indicated by an arrow shown in FIG. 2. This welded part is called an H8 weld line. The upper cylindrical portion of the shroud support 220 is welded to the lower plate portion of the shroud support 220. This welded part is called an H10 weld line.

The entire inner surface of the pressure vessel 210 is covered with a cladding made of stainless steel or the like in order to improve corrosion resistance. The cladding has a thickness of approximately 7 mm to 8 mm. Therefore, portions of the cladding, which are located at the welded parts, are removed. Bases made of INCONEL® are attached to portions (at which the portions of the cladding are removed) of the inner surface of the pressure vessel 210. Then, the outer circumferential side portion of the plate 222, the lower edge portion of the shroud support 220, and the like are welded to the bases.

A rail 230 is provided on the outer circumferential side of the pressure vessel 210 and near the H9 weld line. The rail 230 is provided around the whole circumference of the pressure vessel 210. An ultrasonic probe 101 constitutes a part of the ultrasonic inspection apparatus. The ultrasonic probe 101 is held by a scanning mechanism 104. The scanning mechanism 104 is engaged with the rail 230. The scanning mechanism 104 is capable of slightly pressing the ultrasonic probe 101 toward the outer surface of the pressure vessel 210 and moving along the outer surface of the pressure vessel 210. The ultrasonic probe 101 is capable of transmitting an ultrasonic wave to the H9 weld line to inspect a defect or the like present in the H9 weld line.

As described above, since the cladding made of stainless steel or the like is provided on the inner surface of the pressure vessel 210, irregularity is present on the inner surface of the pressure vessel 210. If an inspection device is placed on the inner surface of the pressure vessel in a similar way to conventional techniques, an efficiency of incidence of an ultrasonic wave on an inspection target may not be constantly maintained due to the irregularity, and a signal received from an inspected portion may vary. This results in difficulty in evaluation of a defect. On the other hand, in the present embodiment, the ultrasonic probe 101 is placed on the side of the outer surface of the pressure vessel 210. Irregularity on the outer surface of the pressure vessel 210 is small, and the efficiency of incidence of the ultrasonic wave on an inspection target can be constantly maintained. In addition, a signal received from an inspected portion does not vary. It is therefore easy to evaluate a defect in the present embodiment.

Furthermore, since the ultrasonic probe 101 is placed on the side of the outer surface of the pressure vessel 210, it is possible to avoid an increase in the size of the ultrasonic probe, unlike a conventional technique in which an ultrasonic probe is placed in water.

In the example shown in FIGS. 1 and 2, only the rail 230 provided near the H9 weld line is shown. However, as described later with reference to FIG. 18, a rail may be provided outside the pressure vessel 210 and near the H11 weld line and may be used to move the ultrasonic probe to ensure that a defect present in the H11 weld line can be detected. A detection of a defect present in the H8 weld line is described later with reference to FIGS. 25A and 25B.

Next, a system configuration of the ultrasonic inspection apparatus according to the present embodiment is described below with reference to FIG. 3.

Figure 3:
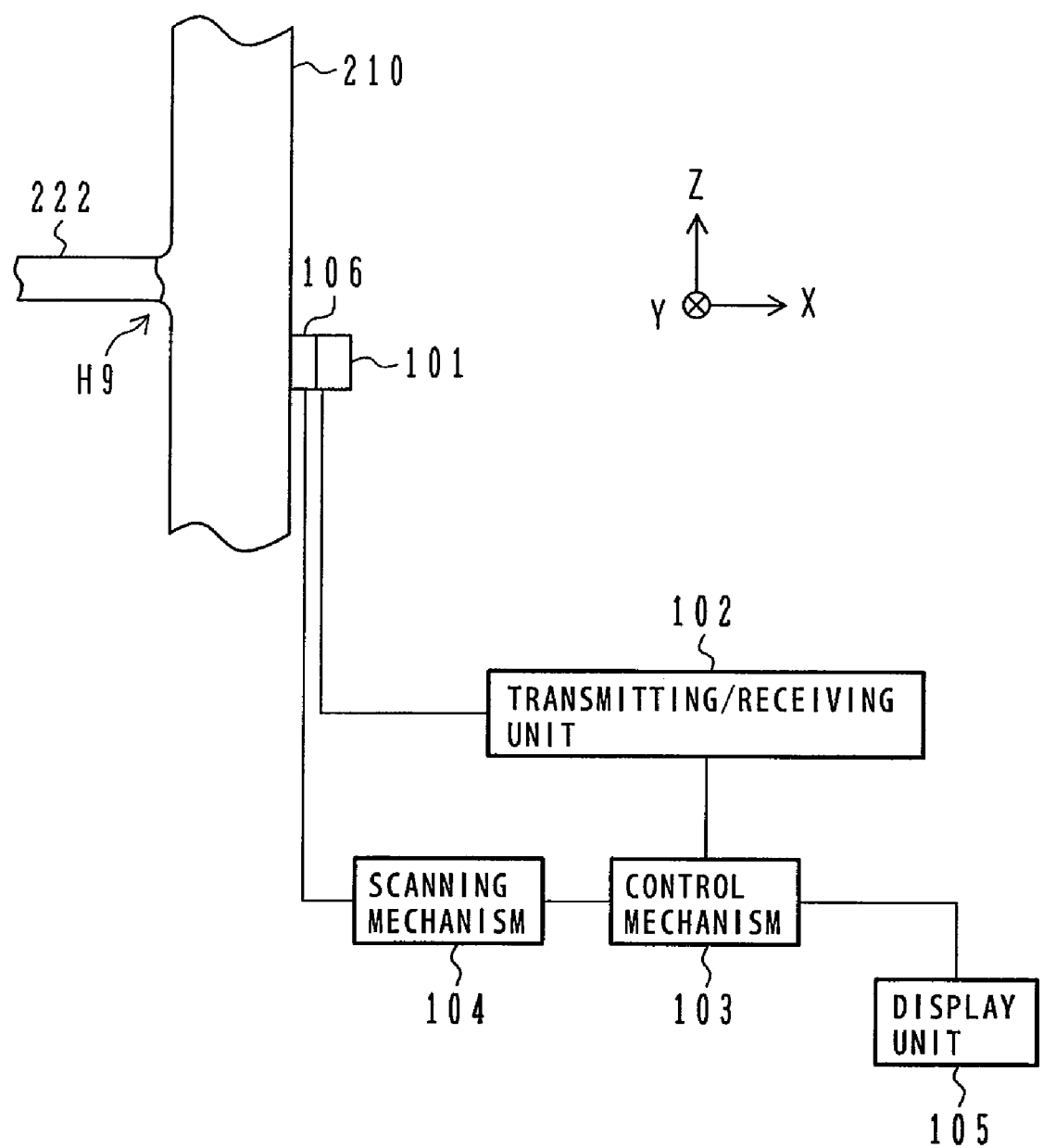
FIG. 3 is a block diagram showing the configuration of the ultrasonic inspection apparatus according to the embodiment of the present invention.

FIG. 3 is a block diagram showing the configuration of the ultrasonic inspection apparatus according to the present embodiment. In FIG. 3, the same reference numerals as those shown in FIGS. 1 and 2 denote the same parts.

In the present embodiment, the ultrasonic probe 101 is pressed toward the outer surface of the pressure vessel 210 and transmits an ultrasonic wave to the H9 weld line to inspect the H9 weld line while incident angles (measured in directions parallel and perpendicular to the direction in which the H9 weld line extends) of the ultrasonic wave on the outer surface of the pressure vessel 210 vary. The ultrasonic probe 101 has a medium 106 attached thereto in order to cause the ultrasonic wave to be incident on the H9 weld line from a direction oblique to the direction (direction of the X axis) of a line or a plane which is normal to the outer surface of the pressure vessel 210. The incidence of the ultrasonic wave on the H9 weld line from the oblique direction is described later with reference to FIGS. 6A and 6B.

In order to improve the efficiency of transmission of the ultrasonic wave to the H9 weld line, a contact medium (or called a couplant) such as water or glycerin is coated or filled between the pressure vessel 210 and the medium 106 as an intermediate medium.

The ultrasonic probe 101 is connected with a transmitting/receiving unit 102. The transmitting/receiving unit 102 has a function for oscillating an excitation voltage used for transmission of the ultrasonic wave and outputting the excitation voltage to the ultrasonic probe 101. In addition, the transmitting/receiving unit 102 has a function for receiving a signal received by the ultrasonic probe 101.

The scanning mechanism 104 causes the ultrasonic probe 101 to one-dimensionally or two-dimensionally scan the outer surface of the pressure vessel 210. The scanning mechanism 104 is controlled by a control mechanism 103 to ensure that the scanning mechanism 104 controls an area to be scanned and a position at which the scanning is performed (or controls the position of the ultrasonic probe 101). Data on the position (position of the ultrasonic probe 101) at which the scanning is performed and a signal received at the position at which the scanning is performed are combined, stored and displayed by a display unit 105.

Next, the configuration of the scanning mechanism 104 used in the ultrasonic inspection apparatus according to the present embodiment is described below with reference to FIG. 4.

Figure 4:
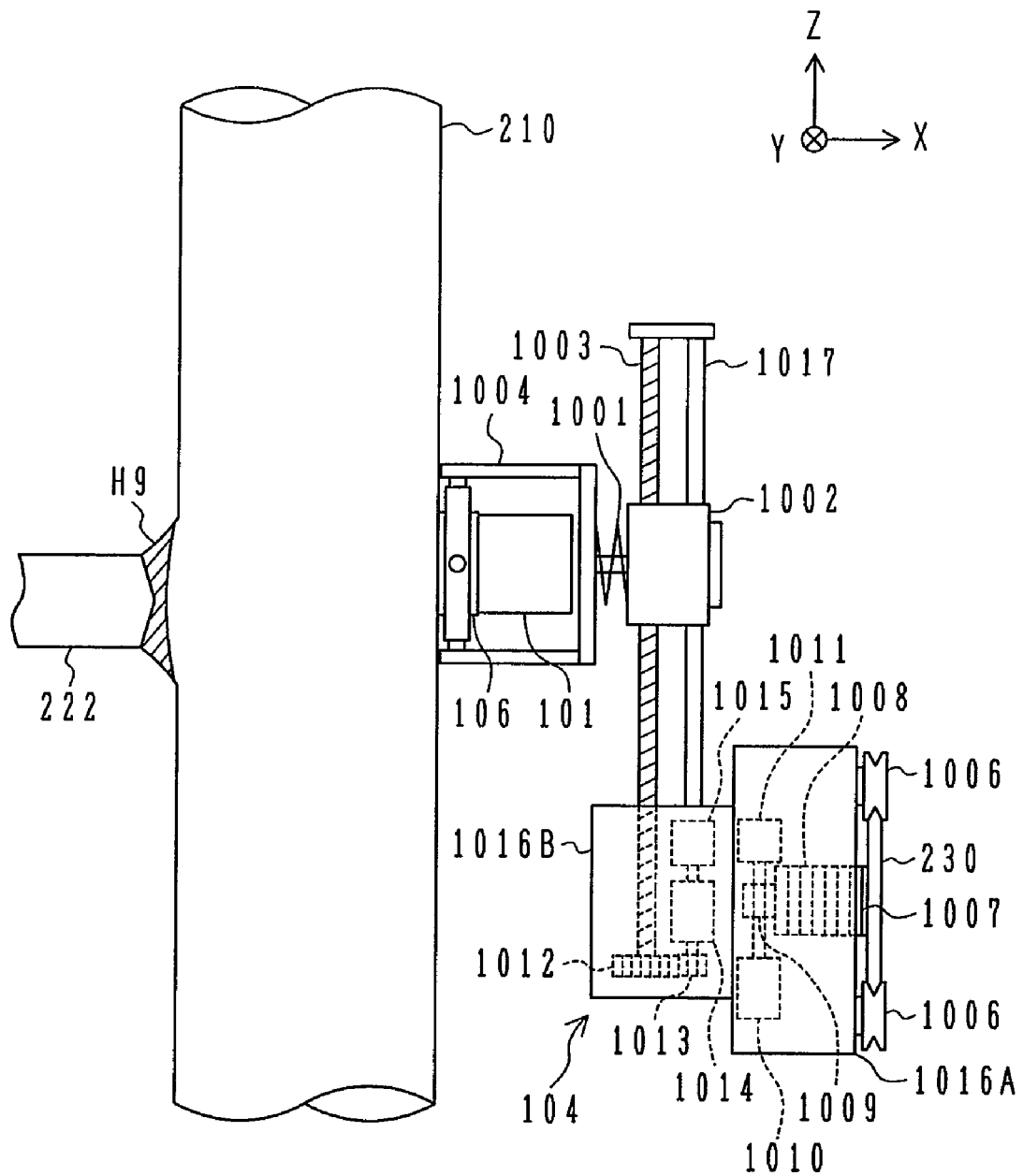
FIG. 4 is a side view of the configuration of a scanning mechanism used in the ultrasonic inspection apparatus according to the embodiment of the present invention.

FIG. 4 is a side view of the scanning mechanism used in the ultrasonic inspection apparatus according to the embodiment of the present invention. In FIG. 4, the same reference numerals as those shown in FIGS. 1 to 3 denote the same parts.

The scanning mechanism 104 is attached to the rail 230 (provided for the inspection and automated ultrasonic testing) by means of a roller 1006. The roller 1006 sandwiches the rail 230 from a vertical direction (direction of the Z axis). A rack 1007 is incorporated in the rail 230.

A case 1016A has the roller 1006, pinions 1008, 1009, a motor 1010 and an encoder 1011 therein. The pinion 1008 interlocks with the rack 1007. The pinion 1008 is rotated by the motor 1010 via the pinion 1009. The motor 1010 is controlled by the control mechanism 103 shown in FIG. 3. The encoder 1011 is directly attached to a shaft of the motor 1010. The encoder 1011 receives positional information with respect to the direction parallel to the H9 weld line and transmits the positional information to the control mechanism 103.

The scanning mechanism 104 can be moved in the direction (direction of the Y axis) parallel to the H9 weld line (direction of the Y axis) by rotating the pinion 1008. That is, the scanning mechanism 104 allows the ultrasonic probe 101 to move in the direction parallel to the H9 weld line.

A case 1016B has a lead screw 1003, a column 1017, pinions 1012, 1013, a motor 1014 and an encoder 1015 therein. A base 1002 is capable of moving along the lead screw 1003 and the column 1017. The base 1002 is coupled with the lead screw 1003. The base 1002 is moved by rotating the lead screw 1003 in the direction (direction of the Z axis) perpendicular to the H9 weld line. In order to rotate the lead screw 1003, the pinion 1012 is attached to an end of the lead screw 1003. The lead screw 1003 is rotated by rotating the pinion 1012. In order to rotate the pinion 1012, the pinion 1013 is attached to the motor 1014 under the condition that the pinion 1013 interlocks with the pinion 1012. The pinion 1012 can be rotated by rotating the motor 1014. The motor 1014 is controlled by the control mechanism 103 shown in FIG. 3. The encoder 1015 is directly attached to a shaft of the motor 1014. The encoder 1015 receives positional information with respect to the direction perpendicular to the H9 weld line and transmits the positional information to the control mechanism 103.

The scanning mechanism 104 can be moved in the direction (direction of the Z axis) perpendicular to the H9 weld line (direction of the Y axis) by rotating the pinion 1012.

The ultrasonic probe 101 is attached to a gimbal mechanism 1004. The gimbal mechanism 1004 is provided to cause the ultrasonic probe 101 to flexibly move along the pressure vessel 210. A pressing mechanism 1001 is provided between the gimbal mechanism 1004 and the base 1002 and adapted to press the ultrasonic probe 101 toward the outer surface of the pressure vessel 210. A spring or an air cylinder may be used as the pressing mechanism 1001, for example.

The scanning mechanism 104 allows the ultrasonic probe 101 to move to a predetermined position of an inspection target and be placed at the predetermined position.

Next, the position of the ultrasonic probe 101 of the ultrasonic inspection apparatus according to the present embodiment and directions of propagation of the ultrasonic wave are described below with reference to FIGS. 5A to 6B.

Figure 5A:
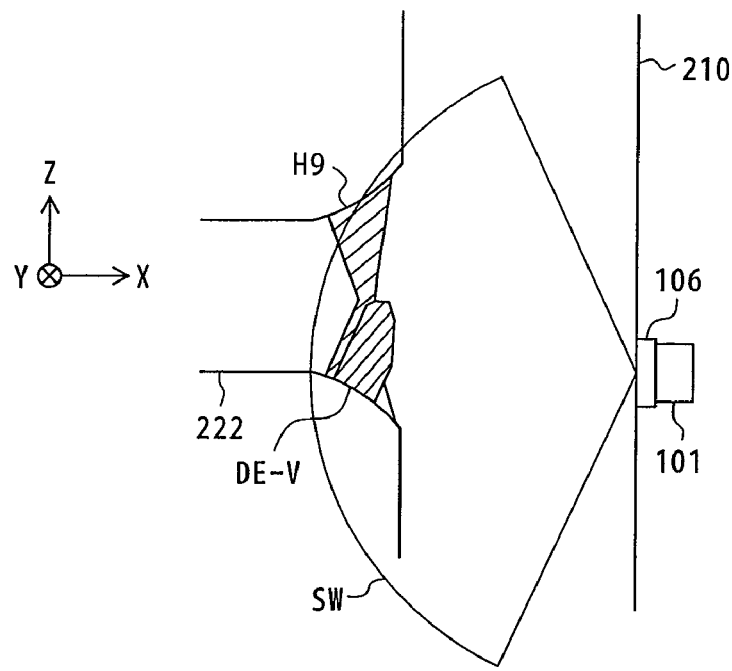
FIGS. 5A and 5B are explanatory diagrams each showing the positional relationship between an H9 weld line and a probe used in the ultrasonic inspection apparatus according to the embodiment of the present invention, and the direction of propagation of an ultrasonic wave.
Figure 5B:
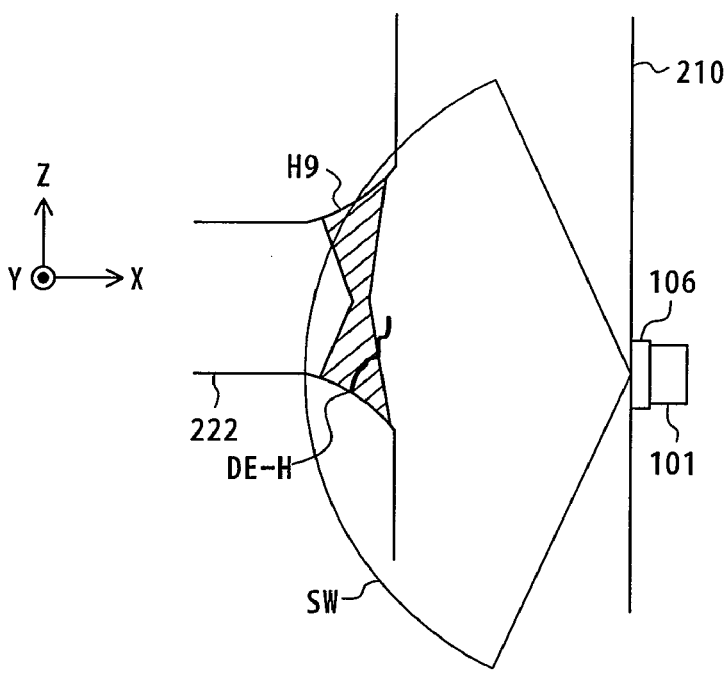
Figure 6A:
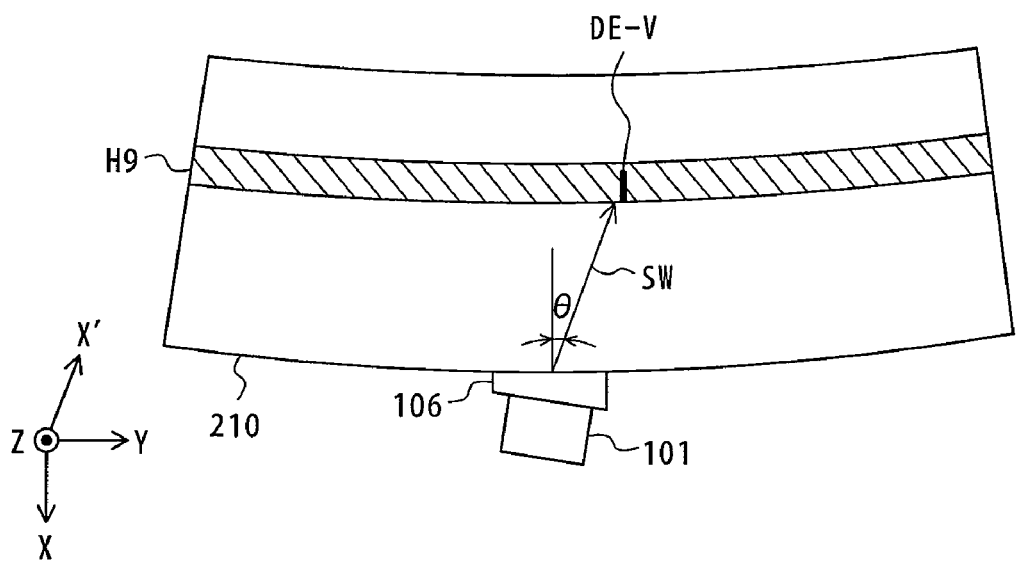
FIGS. 6A and 6B are explanatory diagrams each showing the positional relationship between the H9 weld line and the probe used in the ultrasonic inspection apparatus according to the embodiment of the present invention, and the direction of the propagation of the ultrasonic wave.
Figure 6B:
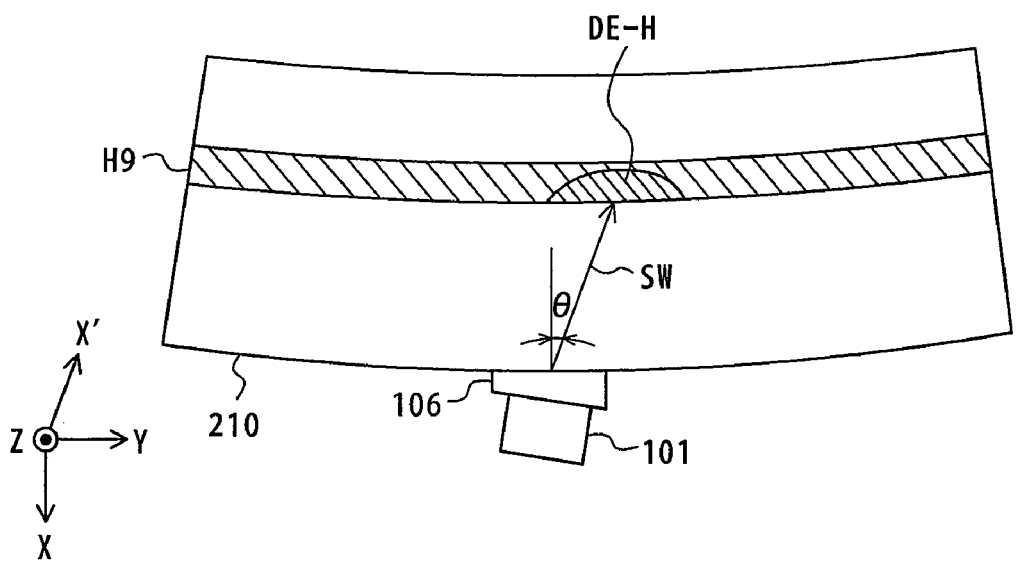

FIGS. 5A to 6B are explanatory diagrams showing the position of the ultrasonic probe 101 of the ultrasonic inspection apparatus according to the embodiment of the present invention and the directions of the propagation of the ultrasonic wave. Each of FIGS. 5A and 5B shows the position of the ultrasonic probe 101 when viewed along a cross section of a wall (having a large thickness) of the pressure vessel 210 and the directions of the propagation of the ultrasonic wave in an X-Z plane. Each of FIGS. 6A and 6B shows the position of the ultrasonic probe 101 when viewed from a top portion of the pressure vessel 210 and directions of the propagation of the ultrasonic wave in an X-Y plane. In FIGS. 5A to 6B, the same reference numerals as those shown in FIGS. 1 to 4 denote the same parts.

The ultrasonic probe 101 transmits an ultrasonic wave SW. The ultrasonic wave SW is incident on the outer surface of the pressure vessel 210 at an optional angle (measured in a direction connecting the top portion of the pressure vessel 210 and a bottom portion of the pressure vessel 210) in the X-Z plane as shown in FIGS. 5A and 5B, and at an optional angle in an X'-Z plane defined by an X' axis and the Z axis, where the X' axis is inclined at an angle θ with respect to a line on a plane which is normal to the outer surface of the pressure vessel 210 as shown in FIGS. 6A and 6B. The ultrasonic probe 101 has the medium 106 to allow the ultrasonic wave to be transmitted at the angle θ with respect to the normal to the outer surface of the pressure vessel 210. The medium 106 may be a shoe made of a material such as acrylic, for example. The angle θ is small and in a range of approximately 10 degrees to 30 degrees. The ultrasonic wave SW is incident at the optional angle in the X-Z plane and incident on an axial crack defect DE-V shown in FIG. 5A at the angle θ in the X-Y plane. Based on an experimental rule, when the angle θ is zero, or when the ultrasonic wave SW is incident on the outer surface of the pressure vessel 210 from the direction of the line or the plane that is normal to the outer surface of the pressure vessel 210, accuracy of detection of the axial crack defect DE-V is reduced. This results from the fact that the axial crack defect extends in a depth direction (direction of the X axis) in many cases. On the other hand, in the present embodiment, since the ultrasonic wave SW is incident on the axial crack defect DE-V from the oblique direction, the accuracy of detection of the axial crack defect DE-V is improved.

In addition, since the ultrasonic wave SW is incident at the angle θ with respect to the normal to the outer surface of the pressure vessel 210 and from the direction oblique to the normal to the outer surface of the pressure vessel 210, it is possible to detect the axial crack defect DE-V and a circumferential crack defect DE-H through a single scanning operation. The ultrasonic wave SW is incident at an optional angle (measured in the direction connecting the top portion of the pressure vessel 210 and the bottom portion of the pressure vessel 210) in the X-Z plane as shown in FIG. 5B, and incident at an optional angle in an X'-Z plane defined by an X' axis and the Z axis, where the X' axis is inclined at the angle θ with respect to the normal to the outer surface of the pressure vessel 210 as shown in FIG. 6B. The ultrasonic probe 101 has the medium 106 to allow the ultrasonic wave to be transmitted from a direction oblique to the normal to the outer surface of the pressure vessel 210. The angle θ is in a range of approximately 10 degrees to 30 degrees. In this case, the ultrasonic probe 101 can receive a signal reflected from the circumferential crack defect DE-H.

The medium 106 can be separable from the ultrasonic probe 101 in FIG. 3. However, the ultrasonic probe 101 and the medium 106 may be integrated with each other.

Next, a method for the scanning with the ultrasonic wave transmitted from the ultrasonic inspection apparatus according to the present embodiment is described below with reference to FIGS. 7 and 8.

Figure 7:
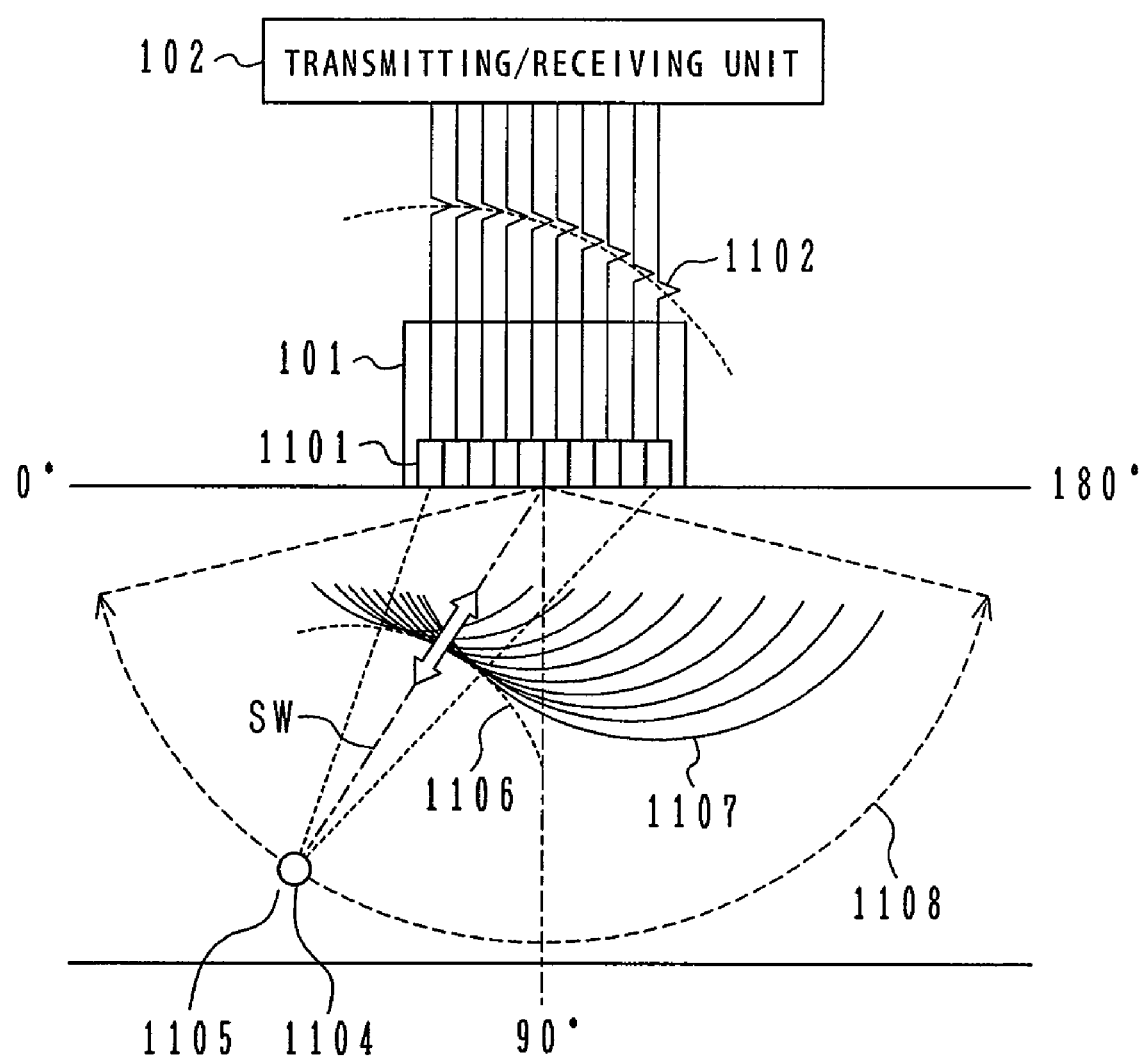
FIG. 7 is an explanatory diagram showing the principle of a method (performed by the ultrasonic inspection apparatus according to the embodiment of the present invention) for transmitting the ultrasonic wave at an optional angle to scan an inspection target.
Figure 8:
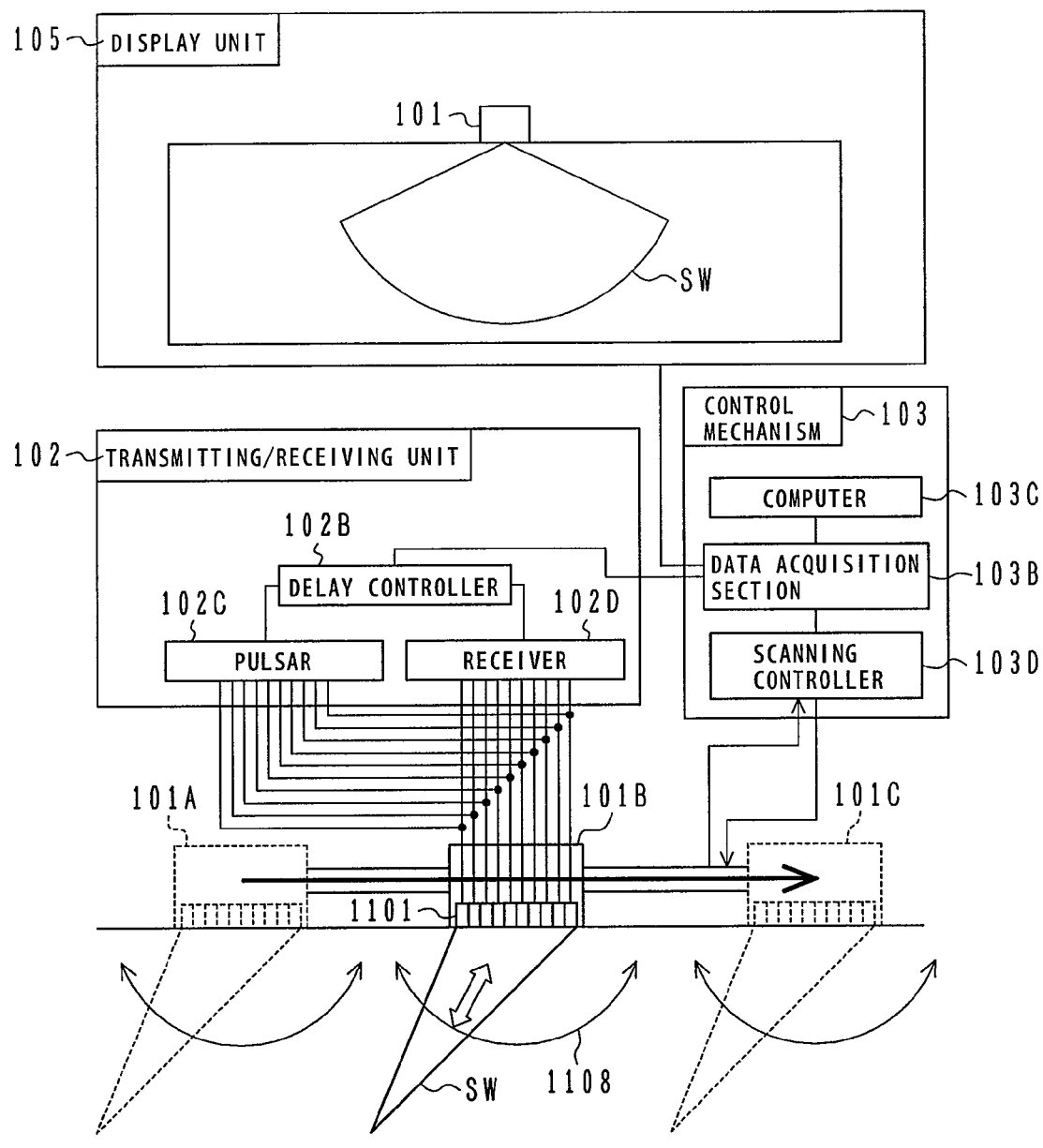
FIG. 8 is a block diagram showing the ultrasonic inspection apparatus according to the embodiment of the present invention, which transmits the ultrasonic wave at an optional angle to scan an inspection target.

FIG. 7 is a diagram showing the principle of a method for setting, to an optional angle, an incident angle at which the ultrasonic wave is transmitted from the ultrasonic inspection apparatus according to the embodiment of the present embodiment. FIG. 8 is a block diagram showing the ultrasonic inspection apparatus that sets the angle at which the ultrasonic wave is transmitted to an optional angle. In FIGS. 7 and 8, the same reference numerals as those shown in FIGS. 1 to 6B denote the same parts.

FIG. 7 shows an outline of a phased array method using an array probe. In order to explain the outline of the phased array method, the medium 106 is not shown in FIG. 7. The array probe is used as the ultrasonic probe 101. The array probe is composed of piezoelectric elements 1101. Typically, the piezoelectric elements 1101 are arrayed in a regular manner, and the number of the piezoelectric elements 101 is several to several tens. As the array probe, a linear array probe having rectangular elements arrayed in a single direction is widely used and known. The size of each of the elements slightly varies depending on the frequency of a voltage applied to the element, but is in a range of several tenth millimeters to several millimeters. The phased array method is to cause the piezoelectric elements 1101 to transmit ultrasonic waves at timings different from each other and receive ultrasonic waves (signals) at timings different from each other in order to combine various ultrasonic beams.

When the phased array method is used, a certain timing pattern (delay pattern) 1102 used for the piezoelectric elements 1101 constituting the array probe 101 is set. Wave fronts 1107 generated from the piezoelectric elements 1101 are combined to form a combined wave front 1106. The combined wave front 1106 propagates to a point 1104 in a direction 1105. Since the wave fronts constituting the combined wave front 1106 intensify with each other at the point 1104, the point 1104 is called a focal point. All sounds generated by the array probe 101 are distributed like the ultrasonic wave SW that is focused on the focal point 1104. The feature of the phased array method is that the distance between the focal point 1104 and the outer surface of the pressure vessel 210, and the propagating direction 1105, are electronically controlled freely and at high speed by changing the delay pattern 1102.

The transmitting/receiving unit 102 transmits information on the delay pattern 1102 to the ultrasonic probe 101. Based on the delay pattern 1102, the ultrasonic probe 101 changes the propagating direction 1105 within a fan shaped region having a spreading angle 1108, for example. The ultrasonic probe 101 transmits and receives an ultrasonic wave at an optional angle while scanning the fan shaped region with the ultrasonic wave. In this example, the single array probe is used to transmit and receive an ultrasonic wave. However, one of two array probes may transmit an ultrasonic wave, while the other of the two array probes may receive an ultrasonic wave.

Next, a description is made of an example of the configuration of the transmitting/receiving unit 102, an example of the configuration of the control mechanism 103, and an example of the configuration of the display unit 105. The transmitting/receiving unit 102 has a delay controller 102B, a pulsar 102C and a receiver 102D. The control mechanism 103 has a computer 103C, a data acquisition section 103B and a scanning controller 103D.

When the phased array method is used, the direction of the propagation of the ultrasonic wave and the position of the focal point can be electronically controlled by providing pulse signals to the elements constituting the array probe 101 at timings different from each other as shown in FIG. 7. The pattern (delay pattern) of the timings is calculated by the computer 103C of the control mechanism 103. Before the calculation, a user inputs parameters (required for the calculation) to the computer 103C through a pointing device or keyboard, for example. The parameters include: an angle of incidence of the ultrasonic wave; a refraction angle; a presence of the focal point; the position of the focal point; and the distance between the focal point and the outer surface of the pressure vessel. The delay controller 102B generates trigger signals and transmits the trigger signals to the pulsar 102C for the respective elements 1101 at times shifted by delay times included in the delay pattern. The pulsar 102C provides a high voltage pulse to each of the elements 1101. The pulsar 102C is connected with each of the elements 1101 constituting the array probe 101. The array probe 101 generates the ultrasonic wave SW to the inside (which is an inspection target) of the pressure vessel 210. In this case, the direction of propagation of the ultrasonic wave SW and the position of the focal point of the ultrasonic wave SW are defined by the delay pattern. When a reflection source is present inside the pressure vessel 210 or on the outer surface of the pressure vessel 210, the ultrasonic wave is reflected in the pressure vessel 210 and reaches the array probe 101.

In this case, the array probe 101 is moved on the outer surface of the pressure vessel 210 (which is the inspection target) by the scanning mechanism 104 to inspect a wide area of the inspection target with the ultrasonic wave.

The ultrasonic wave that reaches the array probe 101 is converted into an electric signal by each piezoelectric element 1101 of the array probe 101. The electric signal is then transmitted to the receiver 102D from each piezoelectric element 1101. The electric signal transmitted by each piezoelectric element 1101 is typically very weak in many cases. Thus, the electric signal transmitted by each piezoelectric element 1101 is amplified to produce a signal having several voltages by an amplifier. After that, each of the amplified signals is converted into a digital signal. The computer 103C receives a position signal from the scanning mechanism 104 through the scanning controller 103D as information on the position of the array probe 101. The signals received by the receiver 102D and the position signal are associated with each other and then stored as digital data in the data acquisition section 103B. The signals that are received by the transmitting/receiving unit 102 and stored with the information on the position of the array probe are displayed by the display unit 105 as a waveform or an image.

Next, a description is made of the relationship between the shape of the weld line and an echo detected by the ultrasonic inspection apparatus according to the present embodiment, with reference to FIGS. 9A to 10B.

FIGS. 9A to 10B are explanatory diagrams each showing the relationship between the shape of the weld line and the echo detected by the ultrasonic inspection apparatus according to the embodiment of the present invention. In FIGS. 9A to 10B, the same reference numerals as those shown in FIGS. 1 to 8 denote the same parts.

Figure 9A:
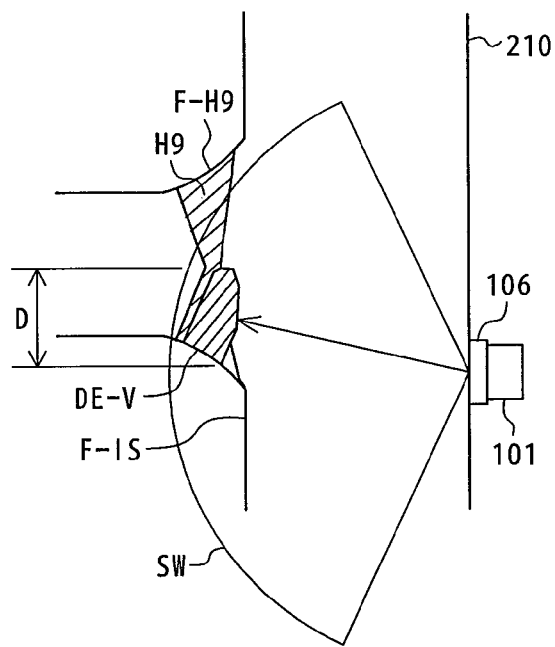
FIGS. 9A and 9B are explanatory diagrams showing the relationship between the shape of the H9 weld line and an echo detected by the ultrasonic inspection apparatus according to the embodiment of the present invention.
Figure 10A:
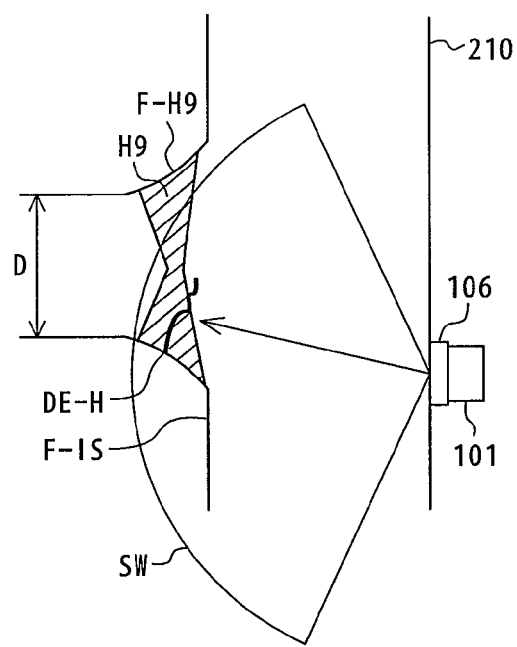
FIGS. 10A and 10B are explanatory diagrams showing the relationship between the shape of the H9 weld line and an echo detected by the ultrasonic inspection apparatus according to the embodiment of the present invention.

Each of FIGS. 9A and 10A shows the positional relationship between the H9 weld line and the ultrasonic probe 101. It is assumed that an axial crack defect DE-V (shown in FIG. 9A) or a circumferential crack defect DE-H (shown in FIG. 10A) is present in the H9 weld line. In the inspection process, it is necessary to detect the axial crack defect DE-V and the circumferential crack defect DE-H and measure the length L of the axial crack defect DE-V and the length L of the circumferential crack defect DE-H. The method for the detection is described later with reference to FIGS. 11 to 14B. The method for measuring the lengths L is described later with reference to FIGS. 16A to 16C.

Figure 9B:
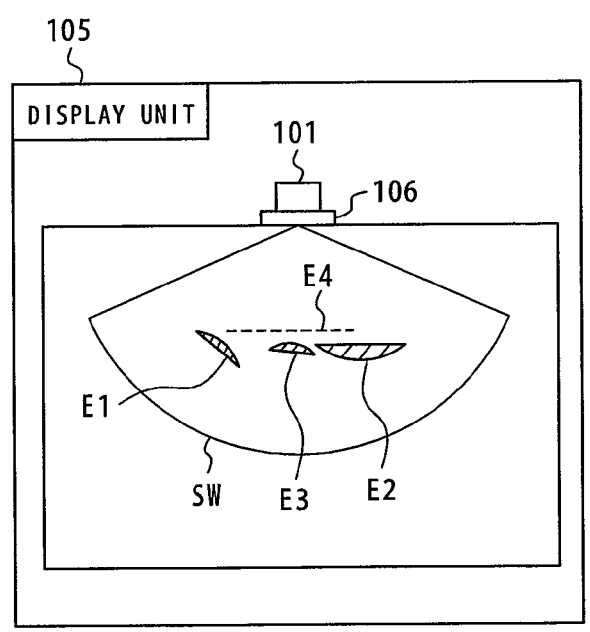

When the H9 weld line and the ultrasonic probe 101 are positioned as shown in FIG. 9A, the ultrasonic probe 101 mainly receives four types of signals. In FIG. 9B, a first echo E1 is an ultrasonic wave reflected from a surface F-H9 of the H9 weld line, and a second echo E2 is an ultrasonic wave reflected from an inner surface F-IS of the pressure vessel 210. A third echo E3 is an ultrasonic wave reflected from the axial crack defect DE-V. A fourth echo E4 is an echo reflected from a boundary between the pressure vessel 210 and the cladding that is provided on the inner surface of the pressure vessel 210 and made of stainless steel or the like.

Figure 10B:
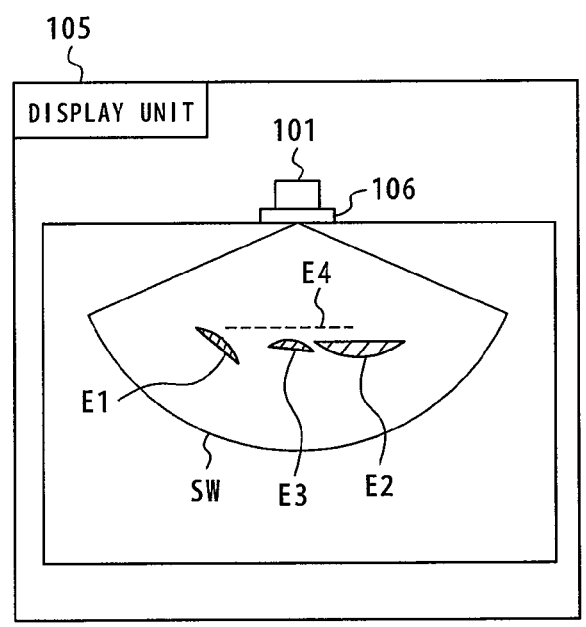

When the H9 weld line and the ultrasonic probe 101 are positioned as shown in FIG. 10A, the ultrasonic probe 101 mainly receives four types of signals. In FIG. 10B, a first echo E1 is an ultrasonic wave reflected from a surface F-H9 of the H9 weld line, and a second echo E2 is an ultrasonic wave reflected from an inner surface F-IS of the pressure vessel 210. A third echo E3 is an ultrasonic wave reflected from the circumferential crack defect DE-H. A fourth echo E4 is an echo reflected from the boundary between the pressure vessel 210 and the cladding that is provided on the inner surface of the pressure vessel 210 and made of stainless steel or the like.

The cross-sectional drawing showing the inspection target is taken along a scan axis direction (parallel to a surface on which the probe 101 inspects the H9 weld line) and a depth direction (perpendicular to the surface on which the probe 101 inspects the H9 weld line). The ultrasonic waves transmitted and received at a plurality of angles are displayed in directions in which the signals are transmitted and received. Therefore, the echoes E1 to E4 are displayed while the positional relationship among the echoes E1 to E4 is maintained.

Next, the inspection method performed by the ultrasonic inspection apparatus according to the present embodiment is described below with reference to FIGS. 11 to 15B.

Figure 11:
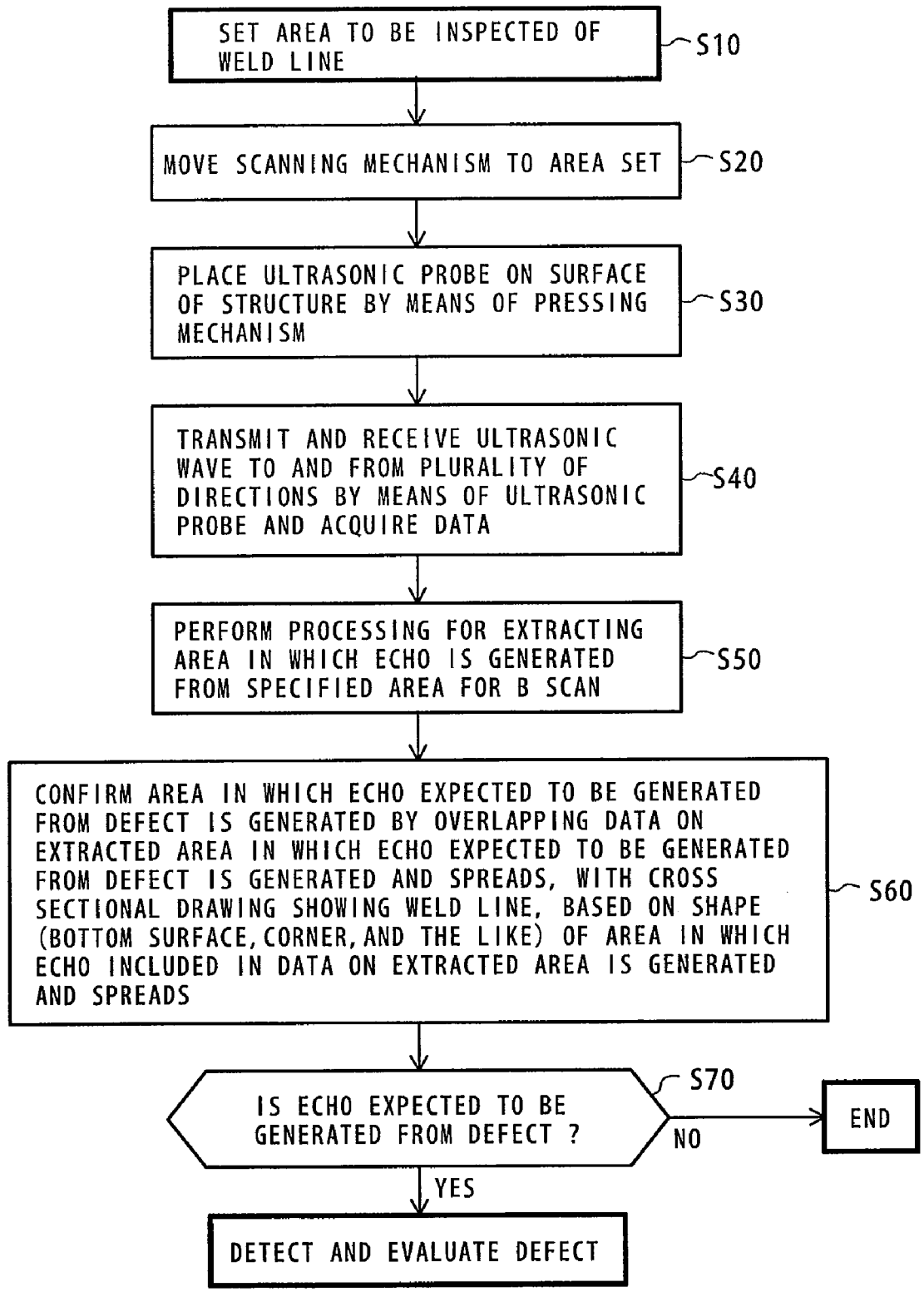
FIG. 11 is a flowchart showing a method for performing an inspection by means of the ultrasonic inspection apparatus according to the embodiment of the present invention.
Figure 12:
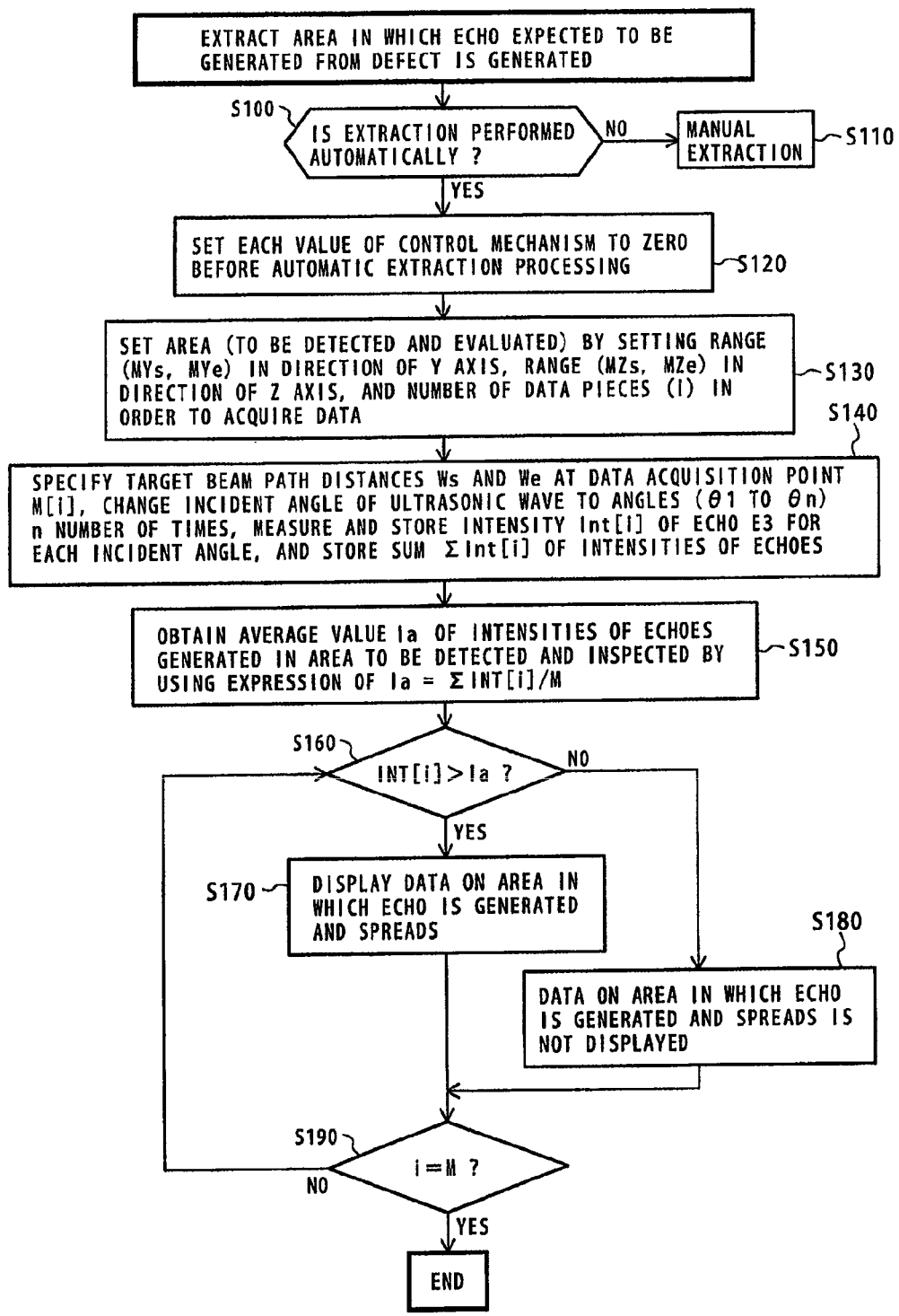
FIG. 12 is a flowchart showing the method for performing the inspection by means of the ultrasonic inspection apparatus according to the embodiment of the present invention.
Figure 14A:
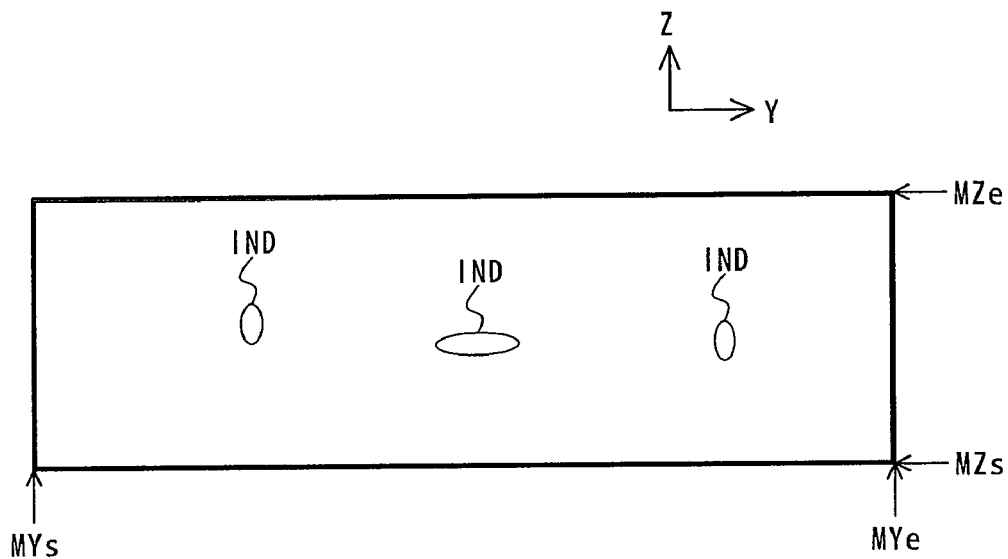
FIGS. 14A and 14B are explanatory diagrams showing the method for performing the inspection by means of the ultrasonic inspection apparatus according to the embodiment of the present invention.
Figure 14B:
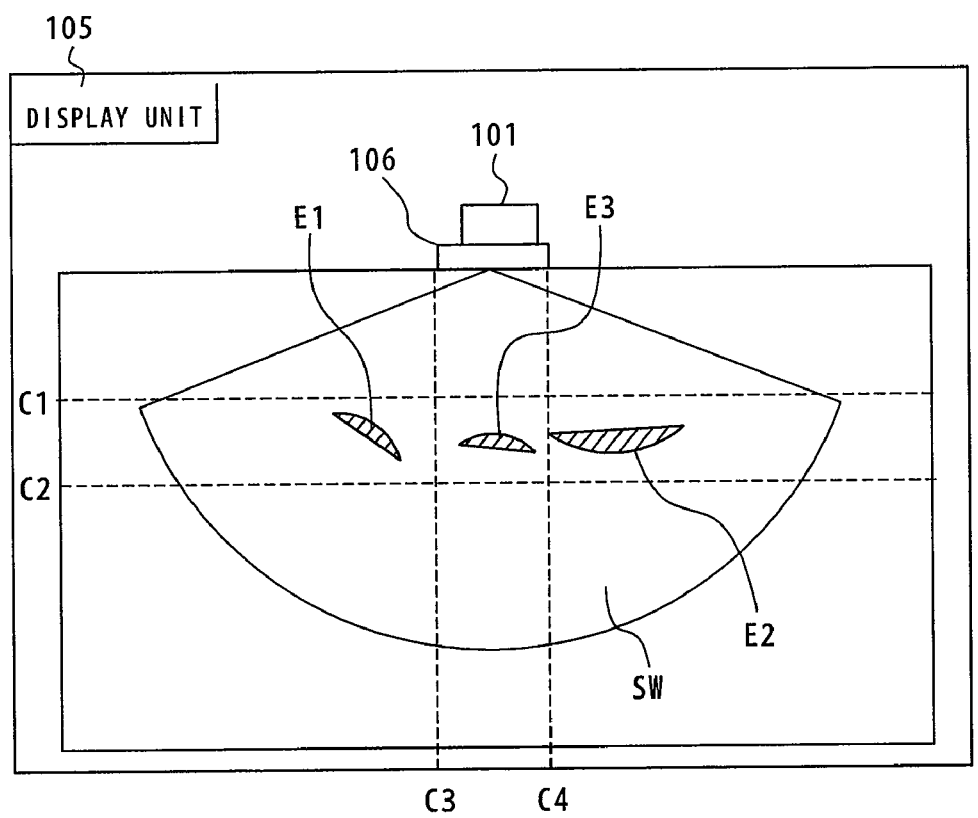
Figure 15A:
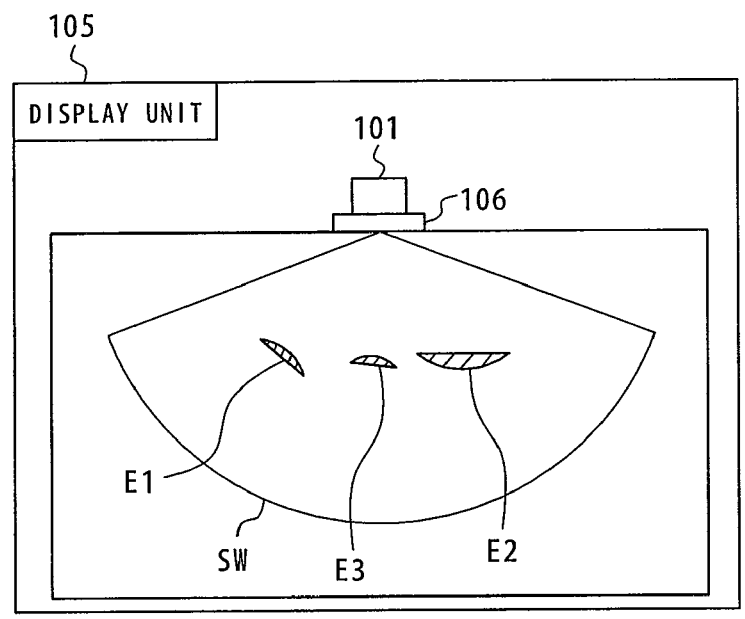
FIGS. 15A and 15B are explanatory diagrams each showing an example of a screen displayed during the inspection performed by the ultrasonic inspection apparatus according to the embodiment of the present invention.
Figure 15B:
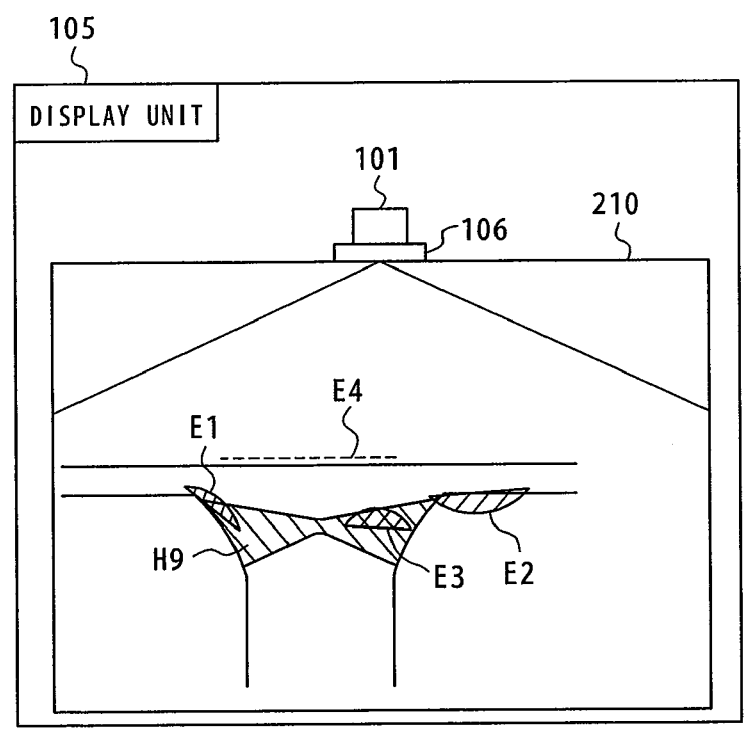

Each of FIGS. 11 and 12 is a flowchart showing the inspection method performed by the ultrasonic inspection apparatus according to the embodiment of the present invention. FIGS. 13A to 14B are explanatory diagrams each showing the inspection method performed by the ultrasonic inspection apparatus according to the embodiment of the present invention. FIGS. 15A and 15B are explanatory diagrams each showing an example of a screen displayed during the inspection performed by the ultrasonic inspection apparatus according to the embodiment of the present invention.

The method for detecting a defect by means of the ultrasonic inspection apparatus according to the present embodiment is described below with reference to FIG. 11.

First, the control mechanism 103 sets an area (to be inspected) of the H9 weld line in step S10 shown in FIG. 11. Next, the control mechanism 103 moves the scanning mechanism 104 to the position of a target area to be inspected in step S20.

Then, the pressing mechanism 1001 presses the ultrasonic probe 101 having the medium 106 attached thereto toward the outer surface of the pressure vessel 210 in step S30.

The control mechanism 103 controls the ultrasonic probe 101 pressed toward the outer surface of the pressure vessel 210 to ensure that the ultrasonic probe 101 transmits an ultrasonic wave in a plurality of directions. When a reflection source is present, the ultrasonic probe 101 receives an echo (reflected wave) from the reflection source. For example, the ultrasonic probe 101 transmits an ultrasonic wave at an optional angle, and an image represented by the ultrasonic wave received by the ultrasonic probe 101 is displayed by the display unit 105.

The ultrasonic probe 101 scans the area to be inspected, and the data acquisition section 103B acquires data obtained in the Z-Y plane at a constant pitch in step S40.

After the data is acquired by the data acquisition section 103B, an area, in which an echo expected to be generated from a defect is generated and spreads, is extracted from the acquired data in step S50. The method for the extraction is described later with reference to FIGS. 12 to 14B.

Next, an area, in which the echo expected to be generated from a defect is generated and spreads is confirmed in step S60 by overlapping or overlaying data on the extracted area in which the echo expected to be generated from a defect is generated and spreads, with the cross-sectional drawing showing the H9 weld line, based on the area (varying depending on the shape of a portion at which the echo is reflected, for example, a bottom surface, a corner, and the like) in which the echo included in the data on the extracted point spreads.

Next, based on the result obtained in step S60, the ultrasonic inspection apparatus determines whether or not the echo expected to be generated from a defect is generated from a defect in step S70. When the ultrasonic inspection apparatus determines that the echo is generated from a defect, the ultrasonic inspection apparatus evaluates that the H9 weld line has a defect.

Next, a description is made of the method (performed in step S50 shown in FIG. 11) for extracting an area in which an echo expected to be generated from a defect is generated and spreads, with reference to FIG. 12.

First, an automatic extraction (of an area in which an echo expected to be generated from a defect is generated and spreads) to be performed by means of the control mechanism 103, or a manual extraction (of an area in which an echo expected to be generated from a defect is generated and spreads), is selected in step S100. When the automatic extraction is selected, a process shown in FIG. 12 proceeds to step S120. When the manual extraction is selected, the process proceeds to step S110. In step S110, the data acquired as shown in FIG. 15A is evaluated while an operator views the display unit 105.

Each value of the control mechanism 103 is set to zero in step S120 before the automatic extraction is performed.

Next, as shown in FIG. 13A, points MYs and MYe defining an area (to be detected and evaluated) in the direction of the Y axis, and points MZs and MZe defining the area (to be detected and evaluated) in the direction of the Z axis are set, and the area (to be scanned) SA defined by the points MYs, MYe, MZs and MZe is set, in step S130.

Figure 13B:
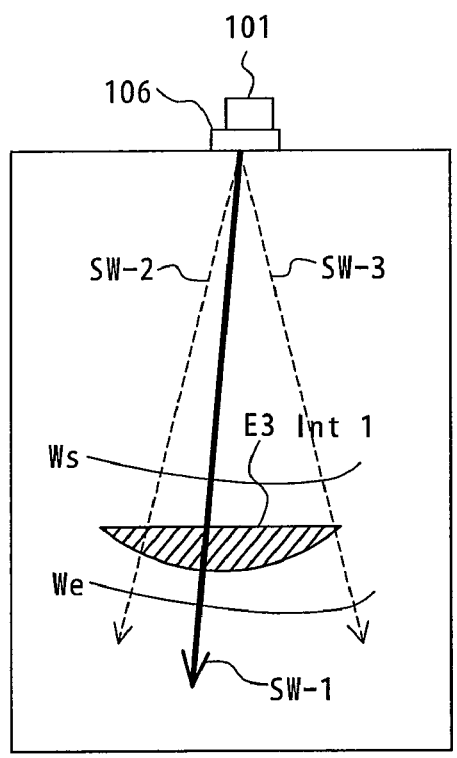
Figure 13C:
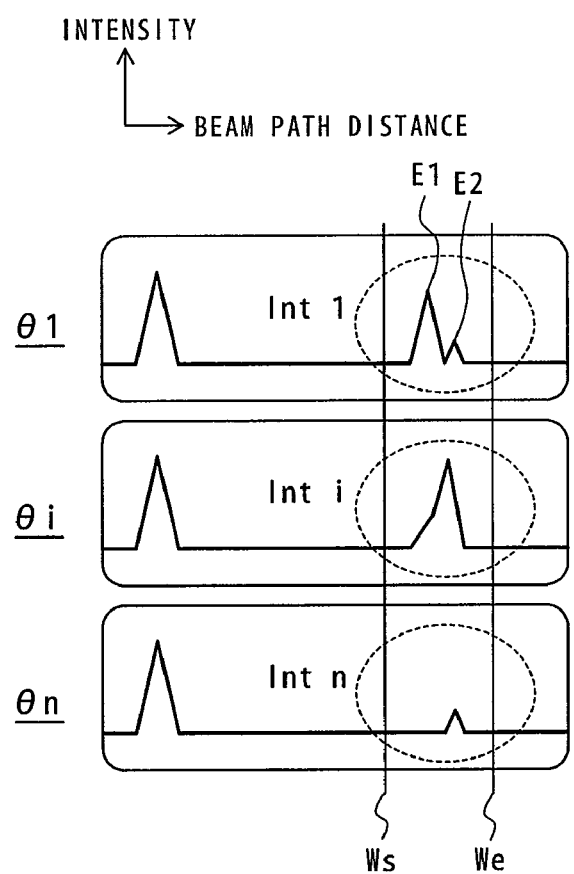

Next, in step S140, as shown in FIG. 13B, target beam path distances Ws and We are specified at a data acquisition point M[i] at which data is acquired by the ultrasonic probe 101. The incident angle of the ultrasonic wave is changed to angles (n number of angles $\theta 1$ to $\theta n$) n number of times. The intensity Int[i] of the echo E3 is obtained for each incident angle. When the ultrasonic wave is incident at an incident angle $\theta i$, and a plurality of echoes is present in the space defined by a difference between the beam path distances Ws and We, the sum of the intensities of the plurality of echoes is represented by Int[i]. For example, when the incident angle is $\theta 1$ shown in FIG. 13C, the following expression is established: Int[1]= E1+E2. Finally, the sum $\Sigma$Int[i] of the intensities Int[i] is obtained. In this example, the area to be detected and inspected is set based on the space defined by the difference between the beam path distances Ws and We and the incident angles ($\theta 1$ to $\theta n$) of the ultrasonic wave. As shown in FIG. 14B, the area to be detected and inspected may be set by using a cursor to surround an area that is displayed by the display unit 105 and defined by C1 to C4.

Next, an average value Ia of the intensities of the echoes generated in the area to be detected and inspected is obtained in step S150.

The intensity Int[i] is compared with the average value Ia in step S160. When Int[i]>Ia, the area in which the echo is generated and spreads due to the ultrasonic wave incident at the incident angle $\theta i$ is displayed, in step S170, on a C scope or the like as shown in FIG. 14A by the display unit 105. It is confirmed whether or not the number i is equal to M in step S190. Steps S160, S170 and S180 are repeated until the number i reaches M.

As shown in FIG. 13A, in the case where the position of the ultrasonic probe 101 is shifted in the direction of the Z axis to ensure that the ultrasonic probe 101 performs the inspection on a plurality of lines, steps S140 to S160 are repeatedly performed for each of the acquired lines.

The intensity of an echo is large at a location where a defect is present in the abovementioned process. The intensity of an echo generated at a point at which a defect is not present is also compared with the average value. It is therefore possible to extract an area in which an echo expected to be generated from a defect is generated and spreads. The extracted area is displayed in a plan view (C scope) shown in FIG. 14A to understand the extracted area. In this example, the average value of the intensities of all echoes is used as a threshold value that is used to compare the intensities of the echoes. An additional threshold value may be set based on the size of a defect to be detected.

As shown in FIG. 15B, the data on the area extracted in step S50 is overlapped or overlaid with the cross-sectional drawing showing the inspection target by the control mechanism 103 in the image displayed by the display unit 105 in step S60 shown in FIG. 11 to confirm the position of a reflection source. The overlap operation is performed by overlapping or overlaying the image shown in FIG. 15A with the cross-sectional drawing shown in FIG. 9A or 10A. During the overlapping or overlaying operation, it is determined whether or not a defect is present by aligning the image with the cross-sectional drawing as shown in FIG. 15B based on the area in which the echo E1 is generated and spreads from the surface of the welded part or on the area in which the echo E2 is generated and spreads from the inner surface of the pressure vessel.

Figure 16A:
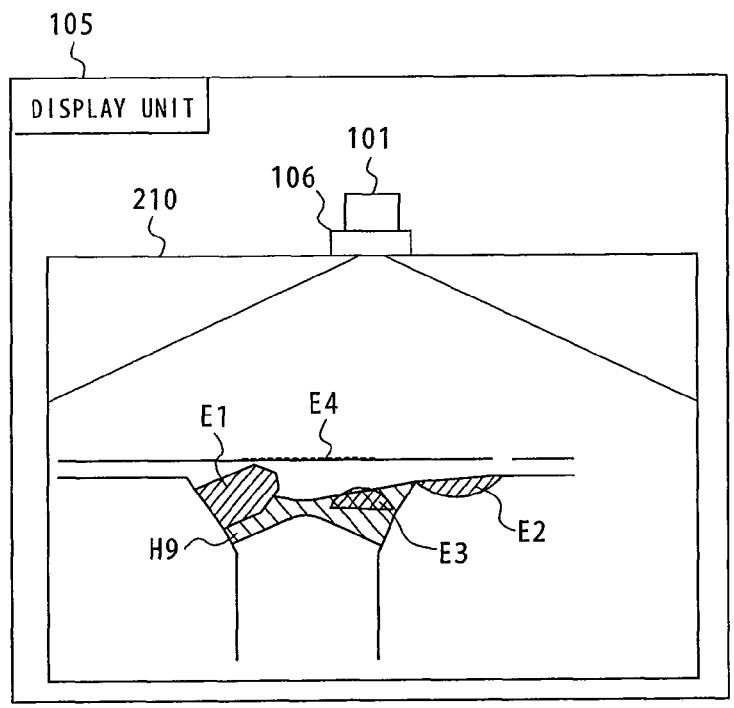
FIGS. 16A to 16C are explanatory diagrams each showing a method for measuring the length of a defect by means of the ultrasonic inspection apparatus according to the embodiment of the present invention.
Figure 16B:
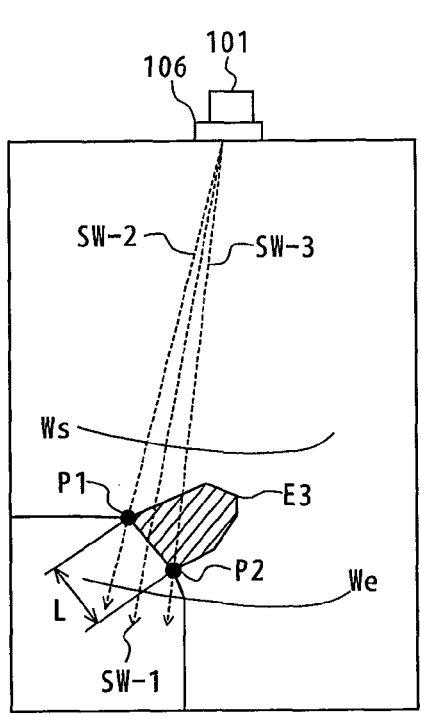
Figure 16C:
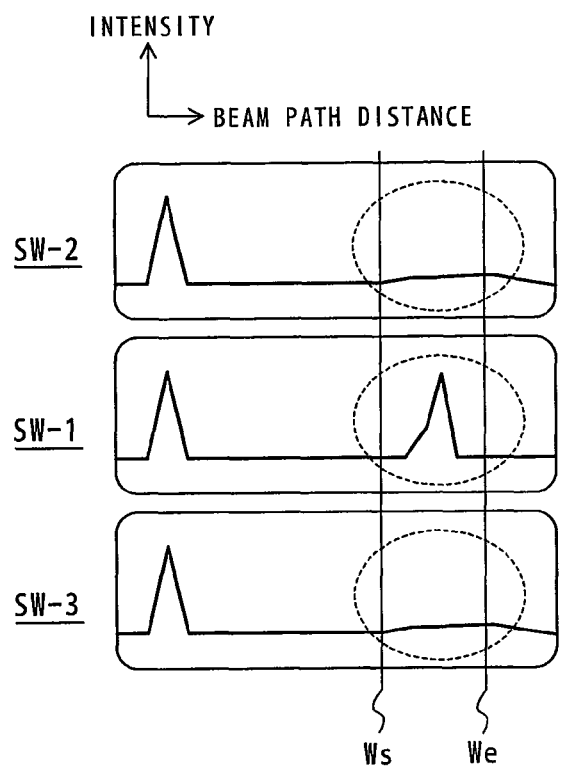

Next, a description is made of a method for measuring the length of a defect by means of the ultrasonic inspection apparatus according to the present embodiment with reference to FIGS. 16A to 16C.

FIGS. 16A to 16C are explanatory diagrams showing the method for measuring the length of a defect by means of the ultrasonic inspection apparatus according to the embodiment of the present invention.

When a defect is detected by the method shown in FIGS. 11 to 15B, the length of the detected defect is measured. A known method is used in order to measure the length of the circumferential crack DE-H. In the known method, the length of the circumferential crack DE-H is measured based on the amount of a movement of the ultrasonic probe 101 in consideration of the intensity of an echo generated from the defect. In this method, however, the length of the axial crack DE-V cannot be measured. The method for measuring the length of the axial crack, according to the present embodiment, is described below.

In FIG. 16A, the measured data and the cross-sectional drawing are overlapped or overlaid with each other to confirm the position of the axial crack DE-V.

As shown in FIG. 16B, a start point P1 and an end point P2, which define a displayed area in which an echo expected to be generated from a point near an opening of the axial crack DE-V is generated and spreads, are measured by changing the incident angle θ of the ultrasonic wave and measuring the intensities of echoes (generated due to ultrasonic waves SW-2 and SW-3 as shown in FIG. 16C) having signal-to-noise ratios of 1 as a threshold.

Next, the start point P1 and the end point P2 are accurately overlapped or overlaid with the cross-sectional drawing. The distance between the start point P1 and the end point P2 is measured on the cross-sectional drawing to measure the length of the axial crack DE-V.

Figure 17:
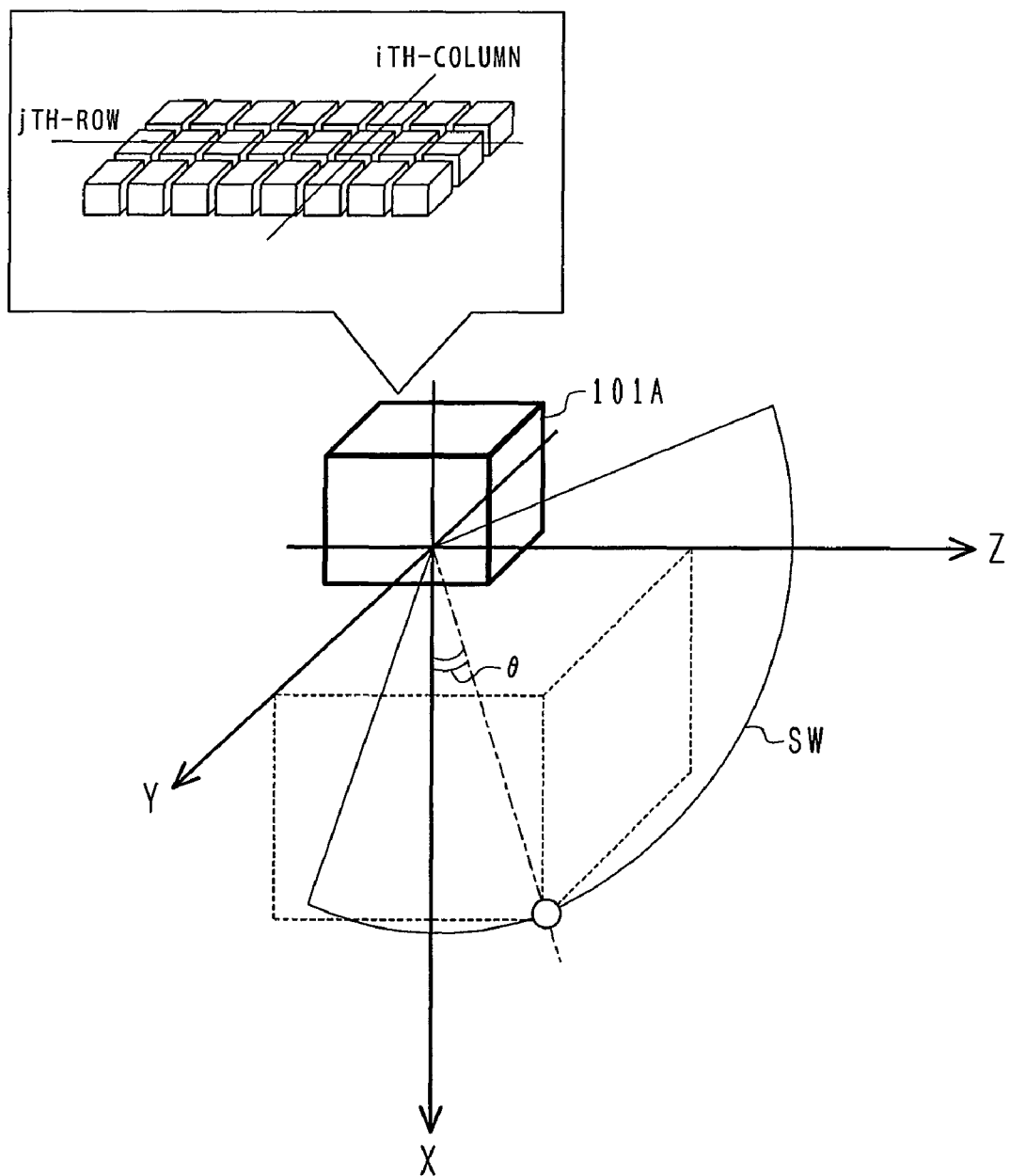
FIG. 17 is a perspective view of another example of the probe used in the ultrasonic inspection apparatus according to the embodiment of the present invention.

Next, a description is made of another example of the ultrasonic probe used in the ultrasonic inspection apparatus according to the present embodiment with reference to FIG. 17.

FIG. 17 is a perspective view of another example of the ultrasonic probe used in the ultrasonic inspection apparatus according to the embodiment of the present invention.

As described above with reference to FIGS. 5A to 6B in the present embodiment, the ultrasonic wave SW is incident at an optional angle in the X-Z plane to scan the inspection target. The ultrasonic wave SW is incident at the angle θ from the direction oblique to the normal to the outer surface of the pressure vessel 210 in the X-Y plane. The medium 106 is used to cause the ultrasonic wave SW to be incident from the oblique direction as shown in FIGS. 6A and 6B.

Even if the medium 106 is not used in order to cause the ultrasonic wave SW to be incident at an optional angle in the X-Z plane and from the oblique direction in the X-Y plane, the same effect as that in the case where the medium 106 is used, can be obtained by using a matrix array probe 101A shown in FIG. 17. The matrix array probe 101A has elements two-dimensionally arrayed. As shown in FIG. 17, the elements arrayed in a j row are used to allow the ultrasonic wave SW to be incident at an optional angle in the X-Z plane in order to scan the inspection target in accordance with the principle shown in FIG. 7, while the elements arrayed in an i column are used to allow the ultrasonic wave SW to be incident at the angle θ and from the oblique direction in the X-Y plane in order to scan the inspection target.

Next, a description is made of the configuration and operations of the ultrasonic inspection apparatus (that inspects the H11 weld line) according to the present embodiment with reference to FIGS. 18 to 22B.

Figure 18:
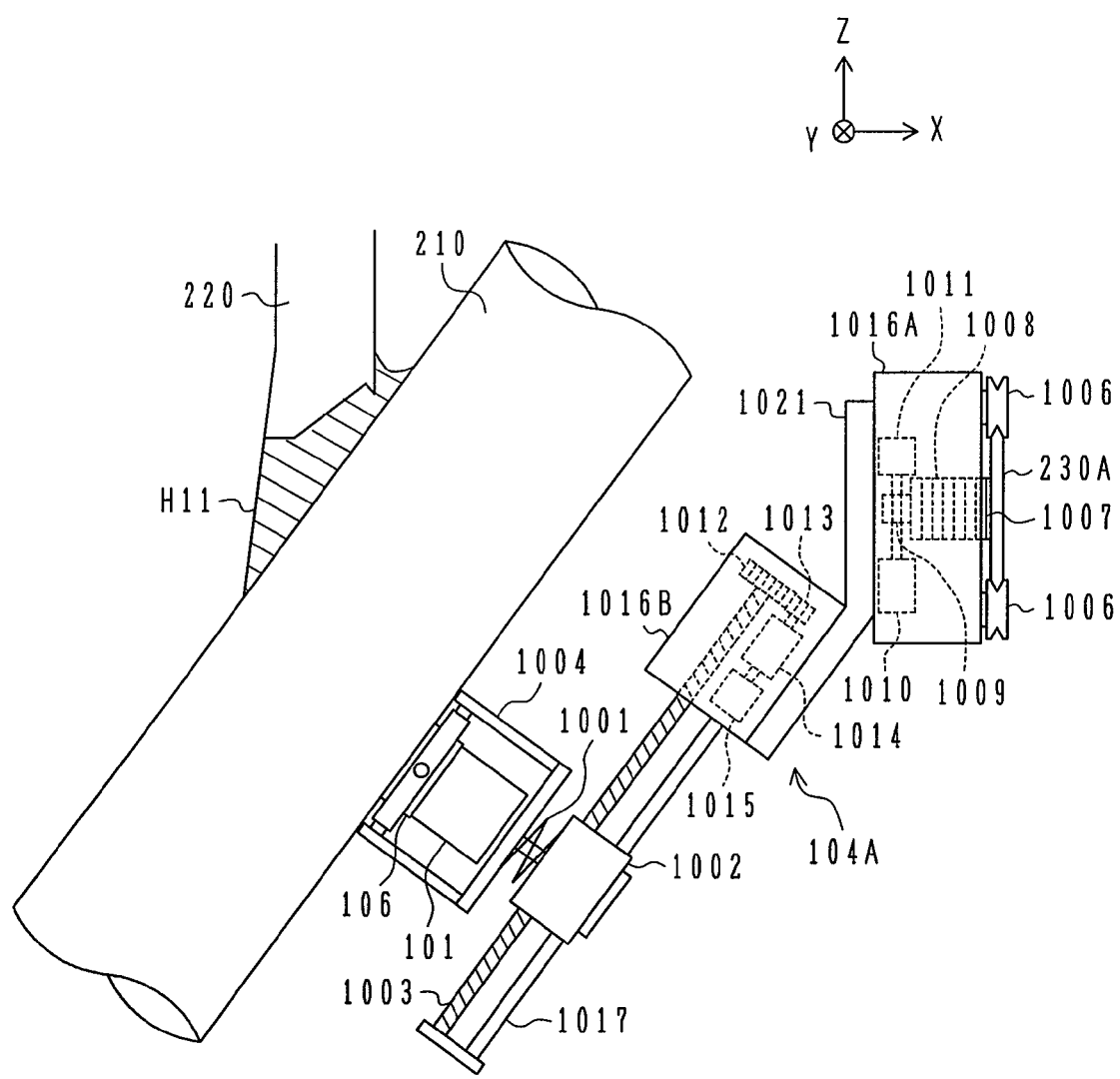
FIG. 18 is a side view of the configuration of the scanning mechanism used in the ultrasonic inspection apparatus (that inspects an H11 weld line) according to the embodiment of the present invention.
Figure 19A:
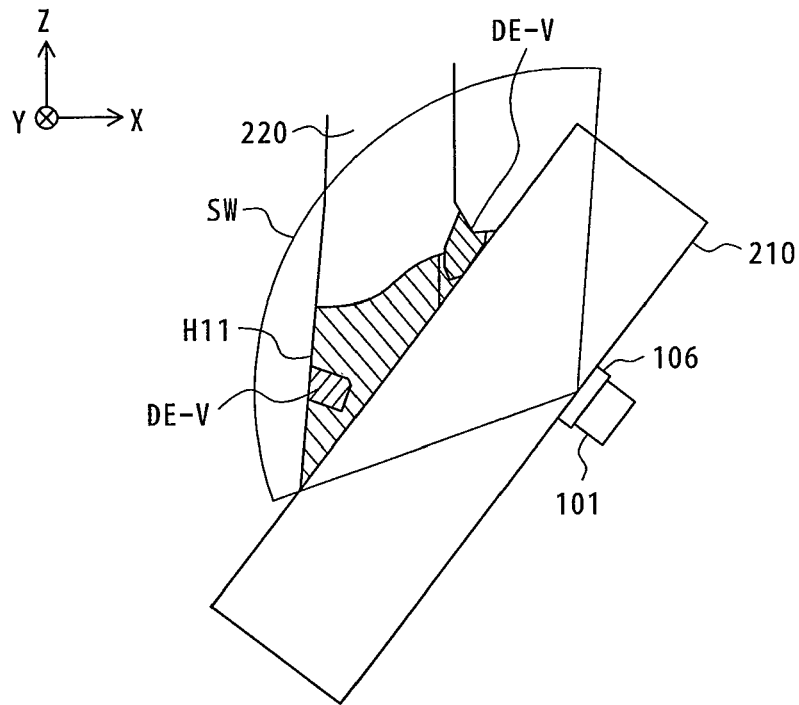
FIGS. 19A and 19B are explanatory diagrams each showing the positional relationship between the H11 weld line and the probe (placed to inspect the H11 weld line) of the ultrasonic inspection apparatus according to the embodiment of the present invention, and the direction of propagation of the ultrasonic wave.
Figure 19B:
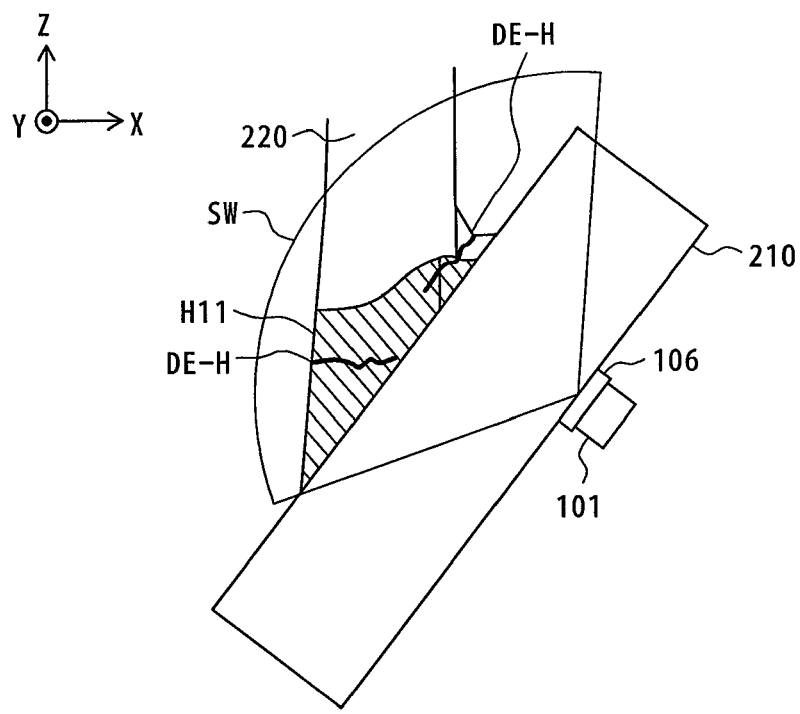
Figure 20A:
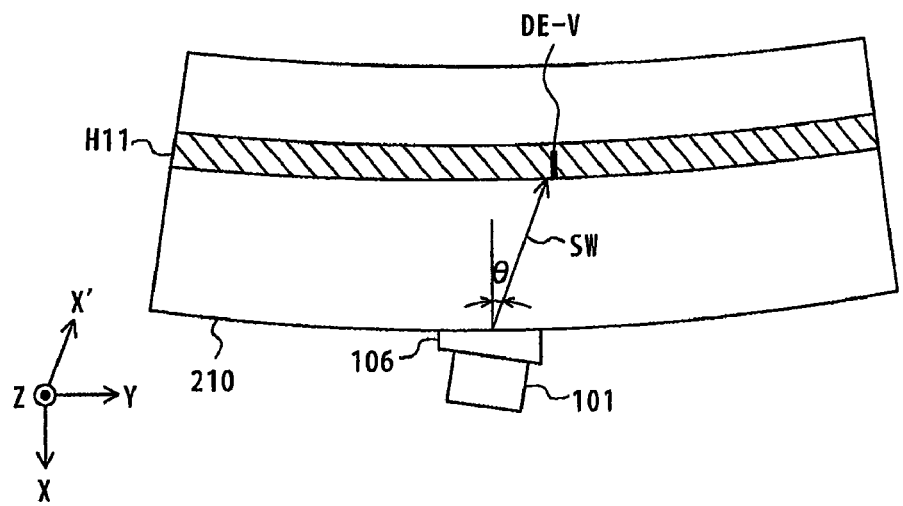
FIGS. 20A and 20B are explanatory diagrams each showing the positional relationship between the H11 weld line and the probe (placed to inspect the H11 weld line) of the ultrasonic inspection apparatus according to the embodiment of the present invention, and the direction of propagation of the ultrasonic wave.
Figure 20B:
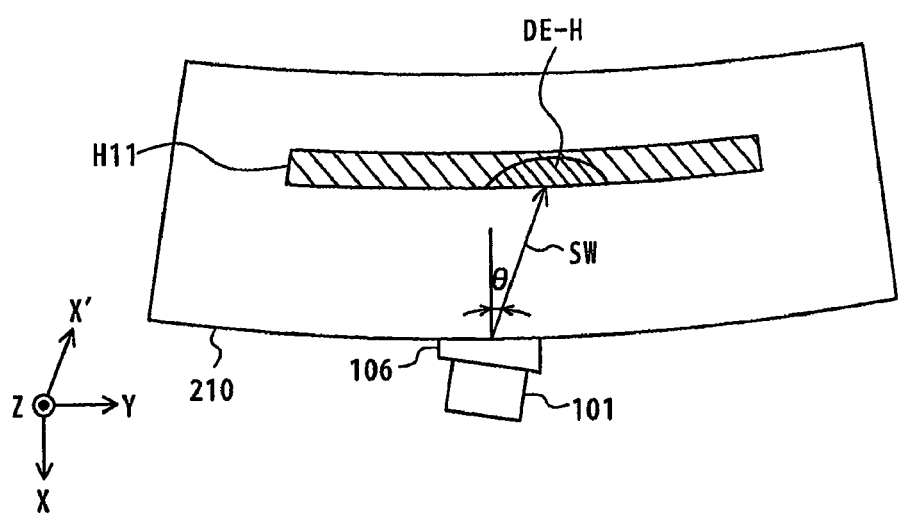
Figure 21A:
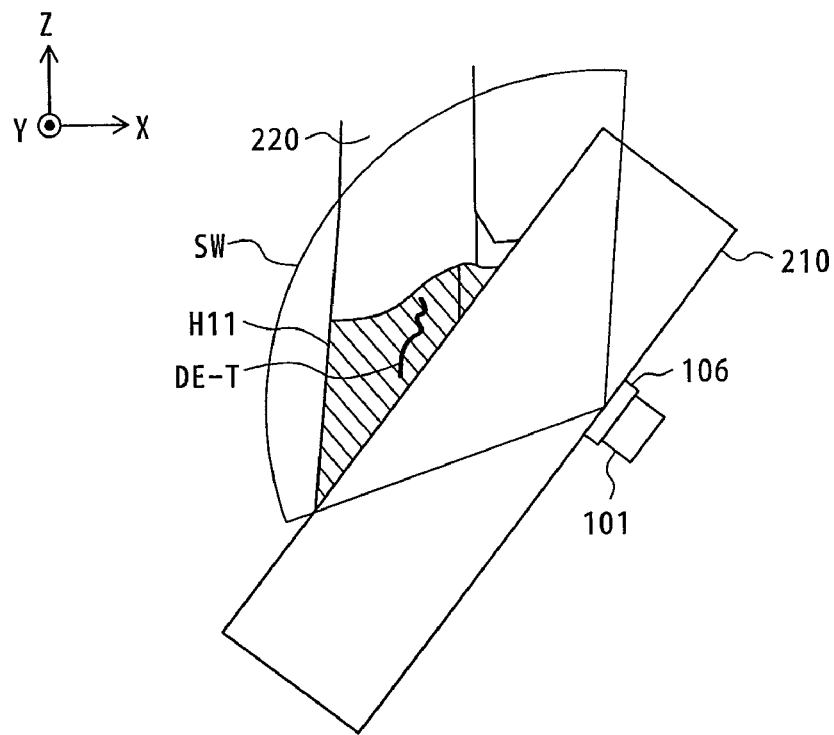
FIGS. 21A and 21B are explanatory diagrams each showing the positional relationship between the H11 weld line and the probe (placed to inspect the H11 weld line) of the ultrasonic inspection apparatus according to the embodiment of the present invention, and the direction of propagation of the ultrasonic wave.
Figure 21B:
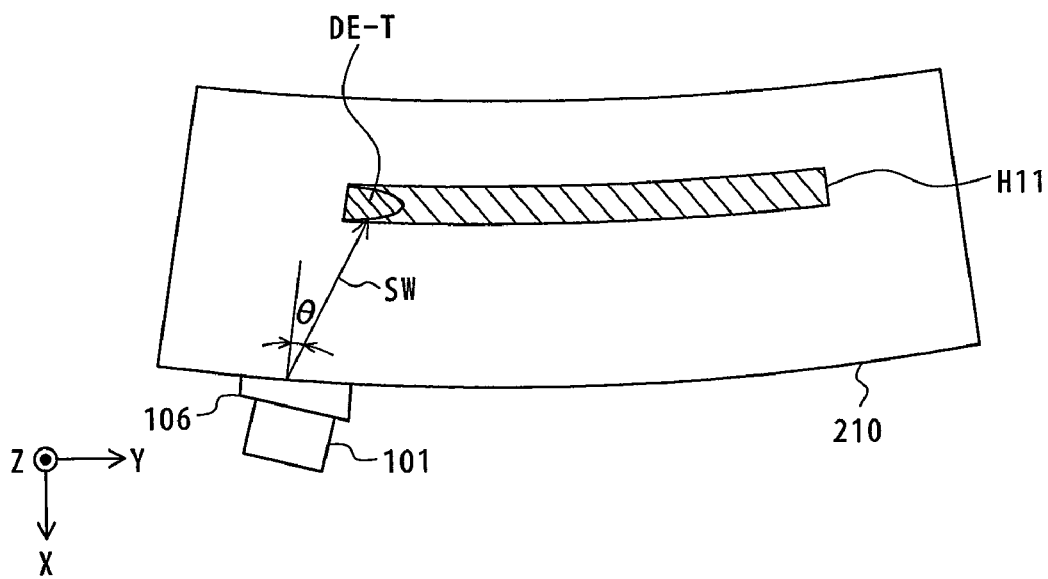
Figure 22A:
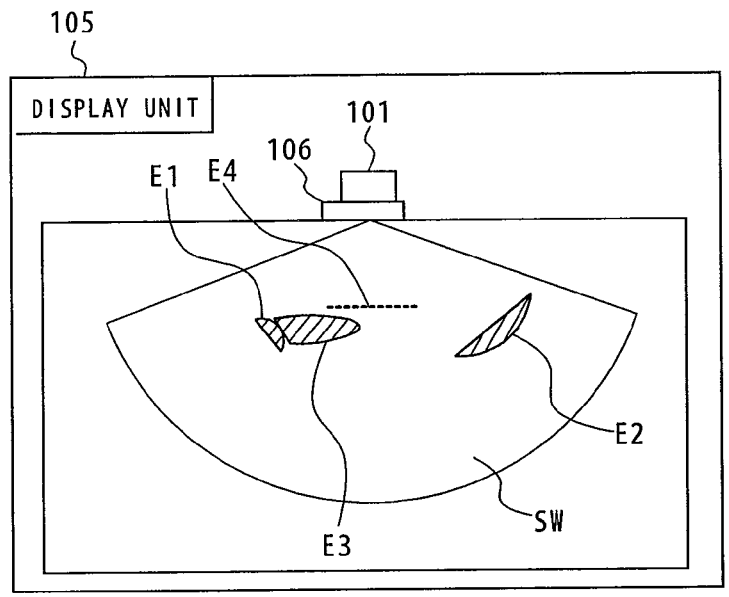
FIGS. 22A and 22B are explanatory diagrams each showing the principle of overlapping performed by the ultrasonic inspection apparatus according to the embodiment of the present invention to inspect the H11 weld line.
Figure 22B:
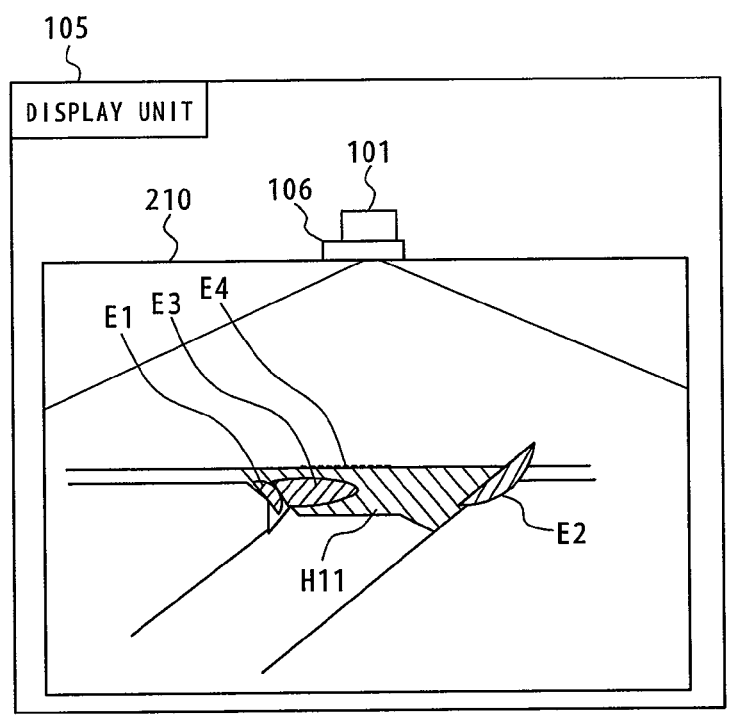

FIG. 18 is a side view of a scanning mechanism 104A used in the ultrasonic inspection apparatus (inspects the H11 weld line) according to the embodiment of the present invention. Each of FIGS. 19 to 21B is an explanatory diagram showing the positional relationship between the H11 weld line and the ultrasonic probe used in the ultrasonic inspection apparatus according to the embodiment of the present invention, and the direction of propagation of the ultrasonic wave. Each of FIGS. 19A, 19B and 21A shows the positional relationship between the H11 weld line and the ultrasonic probe when viewed along the cross section of the wall of the pressure vessel 210, and the direction of the propagation of the ultrasonic wave in the X-Z plane. Each of FIGS. 20A, 20B and 21B shows the positional relationship between the H11 weld line and the ultrasonic probe when viewed from the top portion of the pressure vessel 210, and the direction of the propagation of the ultrasonic wave in the X-Y plane. FIGS. 22A and 22B are explanatory diagrams showing the principle of the overlapping or overlaying performed by the ultrasonic inspection apparatus according to the present embodiment to inspect the H11 weld line. In FIGS. 18 to 22B, the same reference numerals as those shown in FIGS. 1 to 6B denote the same parts.

In order to scan the H11 weld line having a different shape from that of the H9 weld line, it is necessary to improve the scanning mechanism 104. FIG. 18 shows an example of the scanning mechanism 104A that inspects the H11 weld line. The scanning mechanism 104A is attached to a rail 230A that is used to automatically inspect the lower head of the pressure vessel 210 with an ultrasonic wave. Cases 1016A and 1016B are fixed to each other via a coupling plate 1021 in order to position the surface of the medium 106 on the outer surface of the lower head of the pressure vessel 210. This configuration makes it possible to inspect the H11 weld line. Other parts of the scanning mechanism 104A are the same as those of the scanning mechanism 104 shown in FIG. 4.

As shown in FIGS. 20A to 21B, the direction of a line or a plane which is normal to the outer surface (to be scanned) of the pressure vessel 210 is defined as an X axis; the direction in which the weld line extends is defined as a Y axis; the direction perpendicular to the X and Y axes is defined as a Z axis; and an axis obtained by rotating the X axis around the Z axis is defined as an X' axis. The ultrasonic wave is incident on the outer surface of the pressure vessel at an optional angle in an X'-Z plane defined by the X' axis and the Z axis. The medium 106 is provided to allow the ultrasonic wave to be incident on the outer surface of the pressure vessel at an optional angle in the X'-Z plane.

In the method for detecting a defect in the H11 weld line and the method for measuring the length of the defect, the axial crack DE-V (shown in FIG. 20A), the circumferential crack DE-H (shown in FIG. 20B), a crack DE-T (shown in FIG. 21A) formed on a side surface of the H11 weld line, and the like are targeted. These methods can be performed in the same manner as the method for detecting a defect in the H9 weld line and the method for measuring the length of the defect in the H9 weld line. However, since the shape of the H11 weld line is different from that of the H9 weld line, overlapping or overlaying of an image (as shown in FIG. 22A) with a cross-sectional drawing showing an inspection target present in the H11 weld line is described with reference to FIGS. 22A and 22B.

Next, a description is made of the overlapping or overlaying of data on an area in which an echo spreads with the cross-sectional drawing showing the inspection target present in the H11 weld line with reference to FIGS. 22A and 22B. In order to perform the overlapping or overlaying of the data with the cross-sectional drawing, an image as shown in FIG. 22A and the cross-sectional drawing as shown in FIG. 19A or 19B are overlapped or overlaid with each other. The image and the cross-sectional drawing are aligned as shown in FIG. 22B based on areas in which echoes E1 and E2 generated from the surface of the weld part spread, and an area in which an echo E4 generated from the boundary between the pressure vessel 210 and the stainless cladding spreads.

Next, a description is made of the configuration of the ultrasonic inspection apparatus (that inspects the H8 weld line) according to the present embodiment with reference to FIGS. 23 to 28B.

Figure 23:
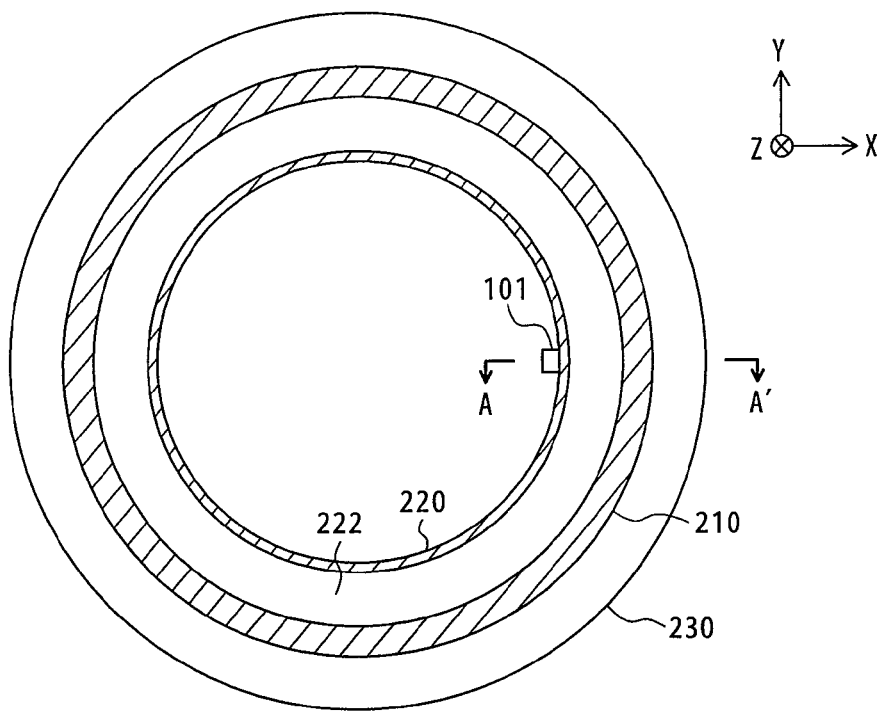
FIG. 23 is a plan view showing the ultrasonic inspection apparatus according to the embodiment of the present invention and shows the state in which the ultrasonic inspection apparatus is installed.
Figure 24:
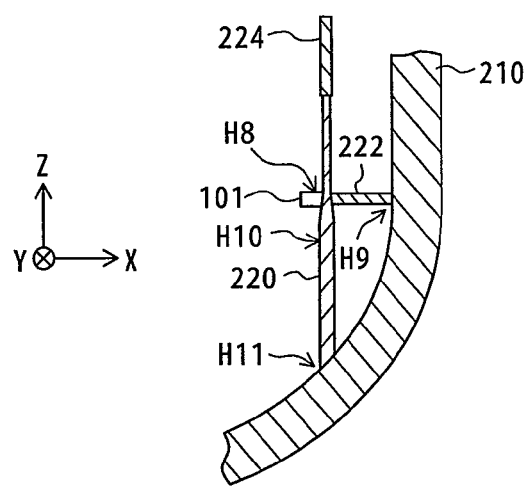
FIG. 24 is a cross-sectional view taken along line A-A' of FIG. 23.

FIGS. 23 and 24 are diagrams each showing the ultrasonic inspection apparatus (that inspects the H8 weld line) according to the embodiment of the present invention and shows the state in which the ultrasonic inspection apparatus is installed. FIG. 24 is a cross-sectional view taken along line A-A' of FIG. 23. In FIGS. 23 and 24, the same reference numerals as those shown in FIGS. 1 to 22B denote the same parts. The H8 weld line is present in the pressure vessel 210 and joins the shroud support 220 and the plate 222. According to the embodiment of the present invention, the ultrasonic probe 101 is placed on the inner surface of the pressure vessel 210 to inspect the H8 weld line, as shown in FIGS. 23 and 24. Specifically, the ultrasonic probe 101 is placed on the surface (i.e., inner surface) of the shroud support 220 located on the opposite side of the H8 weld line to inspect the H8 weld line.

Figure 25A:
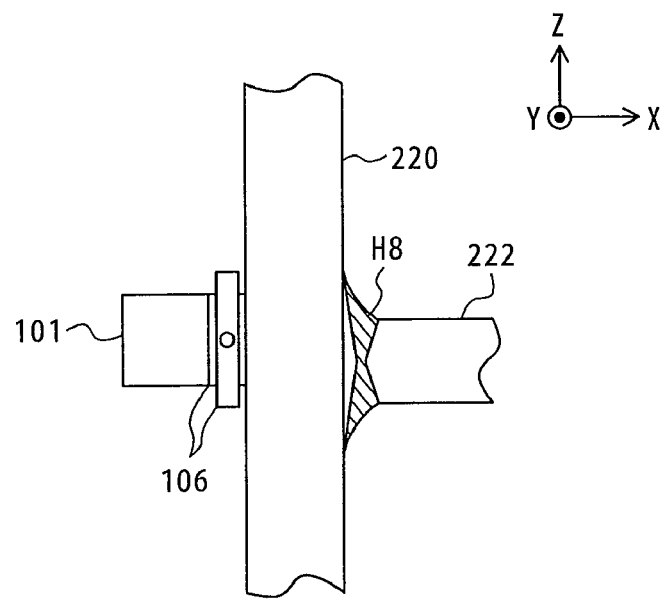
FIGS. 25A and 25B are side views each showing the configuration of the scanning mechanism used in the ultrasonic inspection apparatus that inspects an H8 weld line according to the embodiment of the present invention.
Figure 25B:
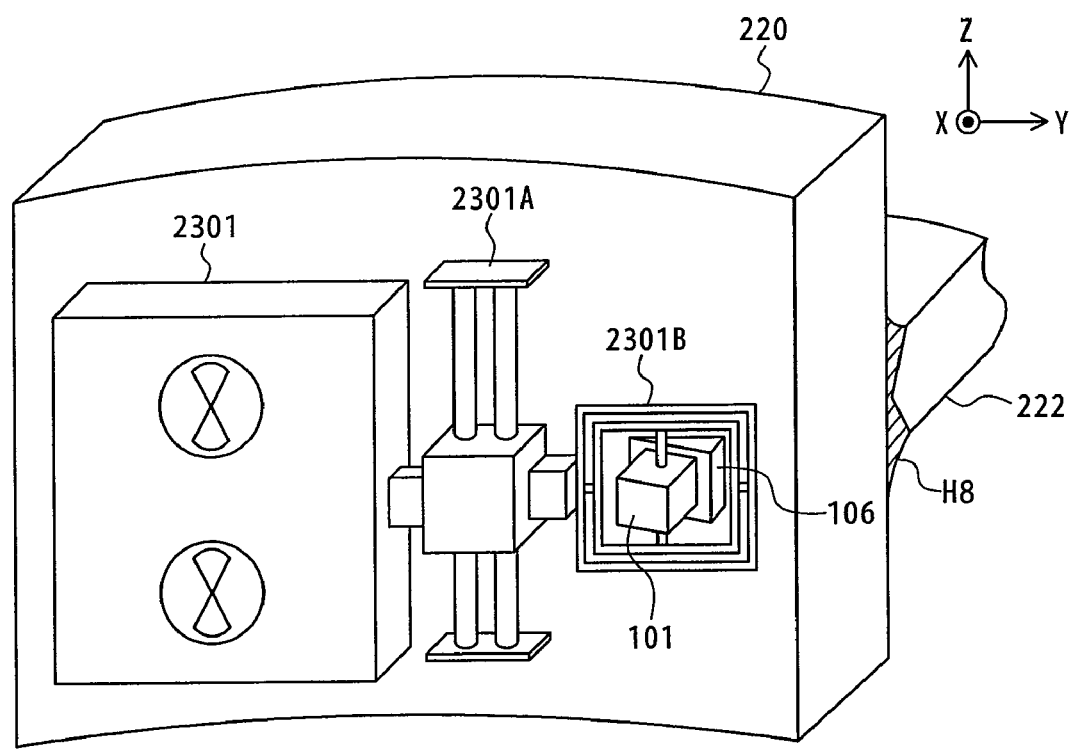

Next, a description is made of an example of the scanning mechanism (used to inspect the H8 weld line) according to the present embodiment with reference to FIGS. 25A and 25B. FIG. 25A is a cross-sectional view of the shroud support 220. FIG. 25B is a perspective view of the shroud support 220 when viewed from the inner surface of the shroud support 220. In FIGS. 25A and 25B, the same reference numerals as those shown in FIGS. 1 to 24 denote the same parts.

Since the H8 weld line is present in the pressure vessel 210, the H8 weld line is covered with a liquid such as pure water in many cases. In this case, a moving device such as a vehicle 2301, which is capable of moving in a liquid, is used to ensure that the ultrasonic probe 101 is capable of inspecting the H8 weld line. The vehicle 2301 has a probe drive mechanism 2301A whose principle is the same as that shown in FIG. 4. The probe drive mechanism 2301A is capable of moving the ultrasonic probe 101 in the directions of the X and Y axes. In addition, the ultrasonic probe 101 is attached to a gimbal mechanism 2301B. The gimbal mechanism 2301B is adapted to flexibly follow the shroud support 220.

Next, a description is made of the positional relationship between the H8 weld line and the ultrasonic probe 101 (that inspects the H8 weld line) according to the present embodiment, and the direction of propagation of the ultrasonic wave with reference to FIGS. 26A to 27B.

Figure 26A:
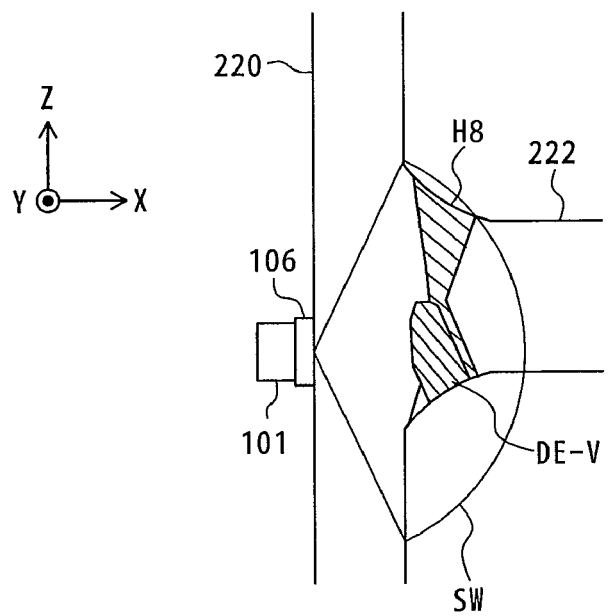
FIGS. 26A and 26B are explanatory diagrams each showing the positional relationship between the H8 weld line and the probe (placed to inspect the H8 weld line) of the ultrasonic inspection apparatus according to the embodiment of the present invention, and the direction of propagation of the ultrasonic wave.
Figure 26B:
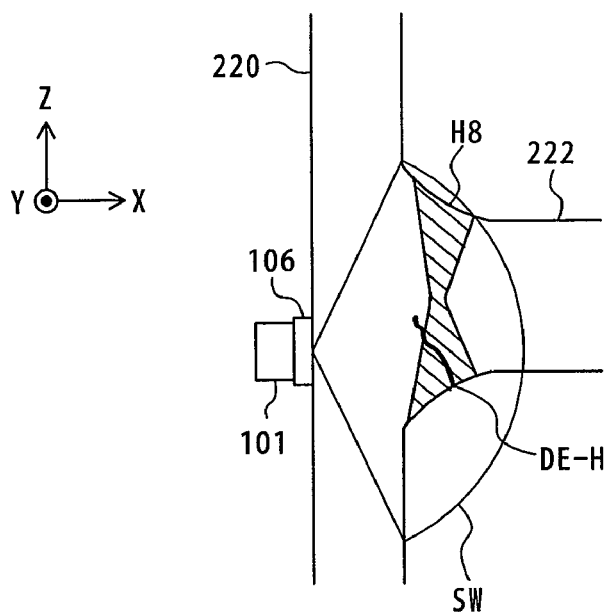
Figure 27A:
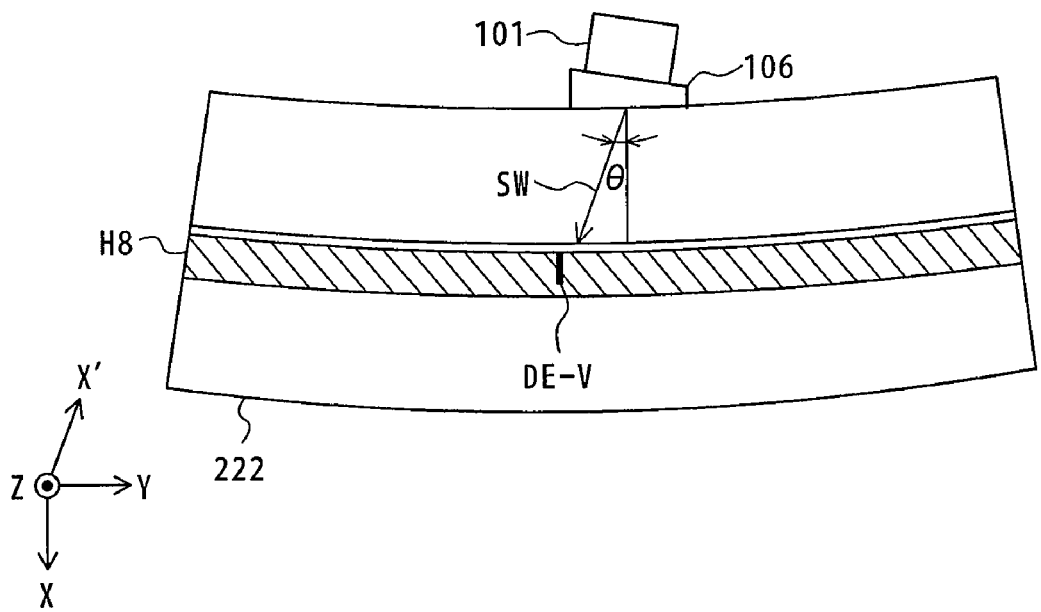
FIGS. 27A and 27B are explanatory diagrams each showing the positional relationship between the H8 weld line and the probe (placed to inspect the H8 weld line) of the ultrasonic inspection apparatus according to the embodiment of the present invention, and the direction of propagation of the ultrasonic wave.
Figure 27B:
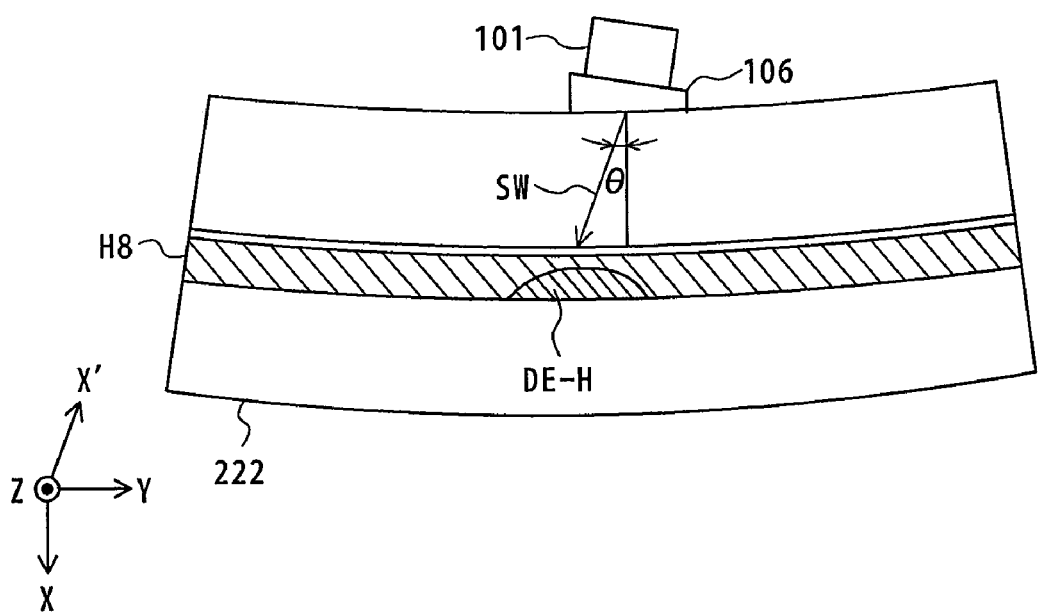

FIGS. 26A to 27B are explanatory diagrams each showing the positional relationship between the H8 weld line and the ultrasonic probe 101 used in the ultrasonic inspection apparatus according to the embodiment of the present invention, and the direction of the propagation of the ultrasonic wave. Each of FIGS. 26A and 26B shows the positional relationship between the H8 weld line and the ultrasonic probe 101 when viewed along a cross section of a wall (having a large thickness) of the shroud support 220, and the direction of the propagation of the ultrasonic wave in the X-Z plane. Each of FIGS. 27A and 27B shows the positional relationship between the H8 weld line and the ultrasonic probe 101 when viewed from a top portion of the shroud support 220, and the direction of the propagation of the ultrasonic wave in the X-Y plane. In FIGS. 26A to 27B, the same reference numerals as those shown in FIGS. 1 to 25B denote the same parts.

As shown in FIGS. 26A and 26B, the ultrasonic wave SW is incident at an optional angle (measured in a direction connecting the top portion of the shroud support 220 and a bottom portion of the shroud support 220) in the X-Z plane to inspect the H8 weld line. On the other hand, as shown in FIGS. 27A and 27B, the ultrasonic wave SW is incident at an angle θ with respect to a line or a plane which is normal to the inner surface of the shroud support 220 and from a direction oblique to the normal to the inner surface of the shroud support 220 in the X-Y plane to inspect the H8 weld line. In other words, the ultrasonic wave SW is incident in an X'-Z plane defined by an X' axis and the Z axis, where the X' axis is inclined at the angle θ with respect to the normal to the inner surface of the shroud support 220. The medium 106 is provided to cause the ultrasonic wave SW to be incident from the oblique direction. The medium 106 is the shoe made of acrylic, for example. The angle θ is small and in a range of approximately 10 degrees to 30 degrees. The ultrasonic wave SW is incident at an optional angle in the X-Z plane and incident on an axial crack defect DE-V shown in FIG. 27A at the angle θ in the X-Y plane. Based on an experimental rule, when the angle θ is zero, or when the ultrasonic wave SW is incident on the inner surface of the shroud support 220 from the direction of the normal to the inner surface of the shroud support 220, accuracy of detection of the axial crack defect DE-V is reduced. This results from the fact that the axial crack defect extends in a depth direction (direction of the X axis) in many cases. On the other hand, in the present embodiment, since the ultrasonic wave SW is incident on the axial crack defect DE-V from a direction oblique to the normal to the inner surface of the shroud support 220, the accuracy of the detection of the axial crack defect DE-V is improved.

In addition, since the ultrasonic wave SW is incident at the angle θ with respect to the normal to the outer surface of the shroud support 220 and from the direction oblique to the normal to the outer surface of the shroud support 220 in the X-Y plane, it is possible to detect the axial crack defect DE-V and the circumferential crack defect DE-H through a single scanning operation. As shown in FIG. 27B, the ultrasonic wave SW is incident in an X'-Z plane defined by an X' axis and the Z axis, where the X' axis is inclined at the angle θ with respect to the normal to the inner surface of the shroud support 220. The ultrasonic probe 101 has the medium 106 to cause the ultrasonic wave to be incident from the direction oblique to the normal to the inner surface of the shroud support 220. The angle θ is in the range of approximately 10 degrees to 30 degrees. In this case, the ultrasonic probe 101 can receive an ultrasonic wave reflected from the circumferential crack defect DE-H.

Figure 28A:
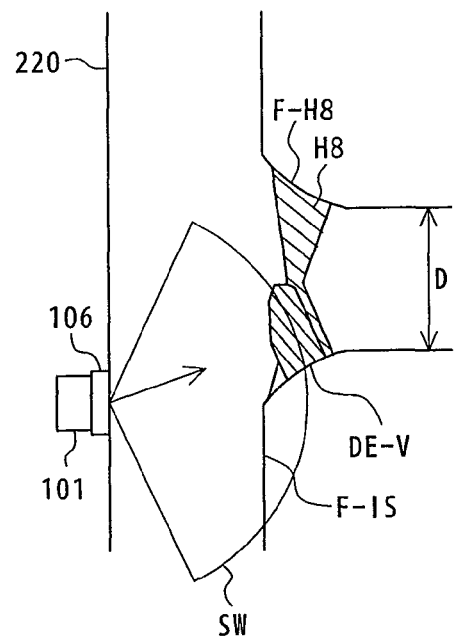
FIGS. 28A and 28B are explanatory diagrams each showing the relationship between the shape of the H8 weld line and an echo detected by the ultrasonic inspection apparatus according to the embodiment of the present invention.
Figure 28B:
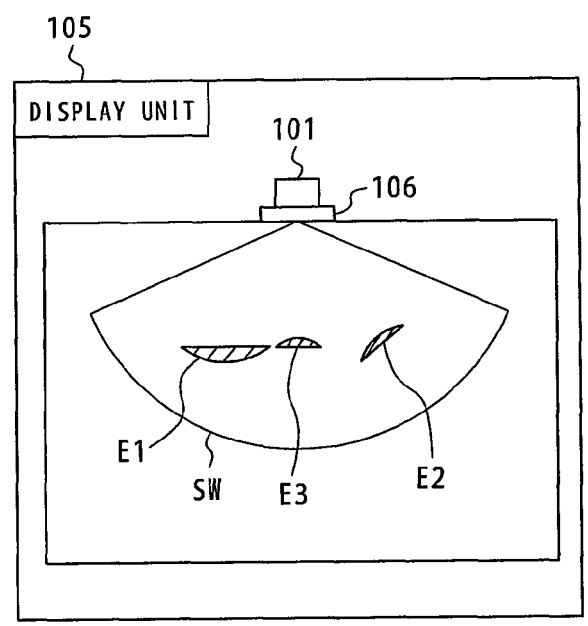

Next, a description is made of the relationship between the shape of the H8 weld line and an echo detected in the ultrasonic inspection apparatus according to the present embodiment with reference to FIGS. 28A and 28B.

When the H8 weld line and the ultrasonic probe 101 are positioned as shown in FIG. 28A, the ultrasonic probe 101 mainly receives three types of signals. In FIG. 28B, a first echo E1 is an ultrasonic wave reflected from a surface F-H8 of the H8 weld line, and a second echo E2 is an ultrasonic wave reflected from an inner surface F-IS of the shroud support 220. A third echo E3 is an ultrasonic wave reflected from the axial crack defect DE-V. The third echo E3 may be an echo reflected from the circumferential crack defect DE-H.

In the method for detecting a defect in the H8 weld line and the method for measuring the length of the defect present in the H8 weld line, the axial crack defect DE-V (shown in FIG. 26A) and the circumferential crack defect DE-H (shown in FIG. 26B) are targeted. These methods can be performed in the same manner as the method for detecting a defect in the H9 weld line and the method for measuring the length of the defect in the H9 weld line. However, since the shape of the H8 weld line is different from that of the H9 weld line, overlapping or overlaying an inspection target area in the H8 weld line with a cross-sectional drawing is described with reference to FIGS. 29A and 29B.

Figure 29A:
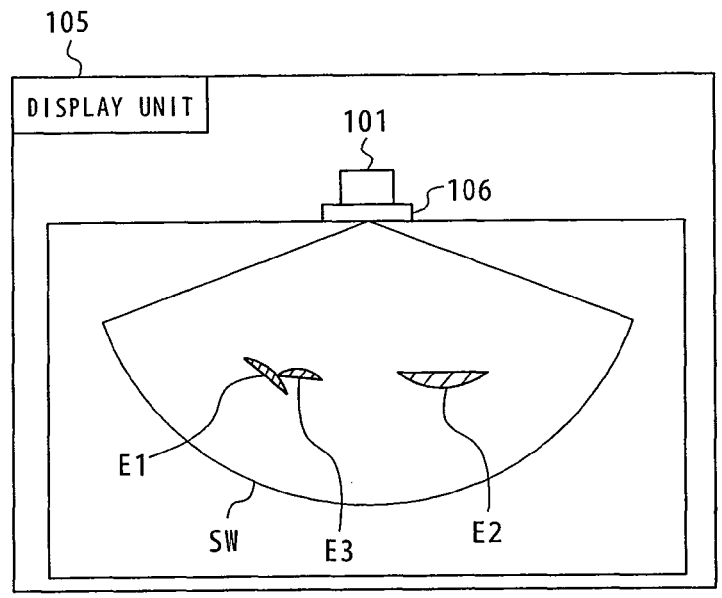
FIGS. 29A and 29B are explanatory diagrams each showing the principle of overlapping performed by the ultrasonic inspection apparatus according to the embodiment of the present invention to inspect the H8 weld line.
Figure 29B:
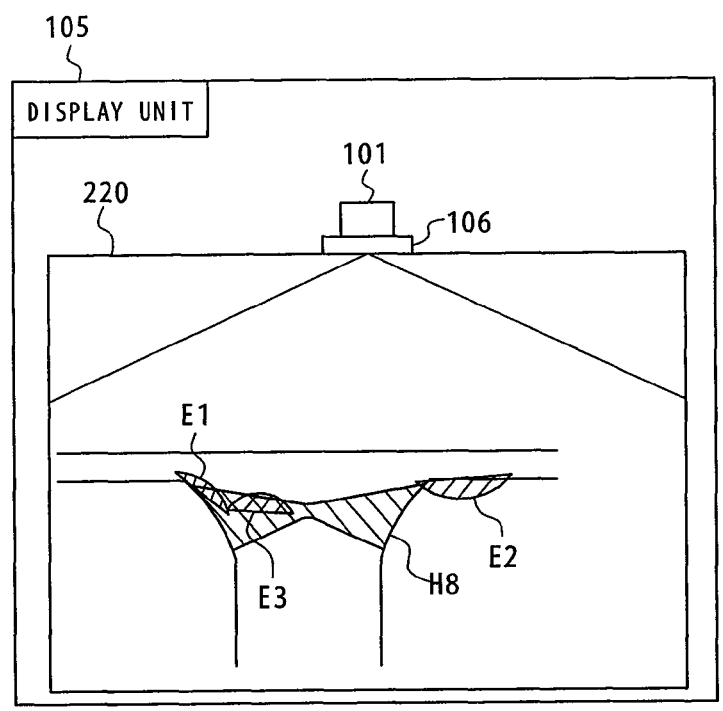

Next, a description is made of the overlapping or overlaying of data on an area in which an echo spreads with the cross-sectional drawing showing the inspection target present in the H8 weld line with reference to FIGS. 29A and 29B. In order to perform the overlapping or overlaying of the data with the cross-sectional drawing, an image as shown in FIG. 29A and the cross-sectional drawing as shown in FIG. 26A or 26B are overlapped or overlaid with each other. The image and the cross-sectional drawing are aligned as shown in FIG. 29B based on areas in which the echoes E1 and E2 generated from the surface of the weld part spread and the like. The cross-sectional drawing showing the inspection target is taken along a scan axis direction (parallel to a surface on which the ultrasonic probe 101 inspects the H8 weld line) and a depth direction (perpendicular to the surface on which the ultrasonic probe 101 inspects the H8 weld line). The ultrasonic waves transmitted and received at a plurality of angles are displayed in directions in which the signals are transmitted and received. Therefore, the echoes E1 to E3 are displayed while the positional relationship among the echoes E1 to E3 is maintained.

Next, a description is made of the positional relationship between a weld line and the ultrasonic probe (used in the ultrasonic inspection apparatus according to the present embodiment) placed on an outer surface of a tube to inspect the weld line, and the direction of propagation of the ultrasonic wave, with reference to FIGS. 30A to 31B.

In FIGS. 1 to 29B, the ultrasonic probe is placed on the outer surface of the structure (pressure vessel) having the cylindrical shape to inspect the H9 weld line and the H11 weld line, and placed on the inner surface of the structure (pressure vessel) having the cylindrical shape to inspect the H8 weld line. In FIGS. 1 to 29B, a large structure (pressure vessel having a diameter of 5 meters or more) is used as an example.

On the other hand, the present embodiment can be applied to a typical tube (as shown in FIGS. 30A to 31B) having a diameter of less than 1 meter.

Figure 30A:
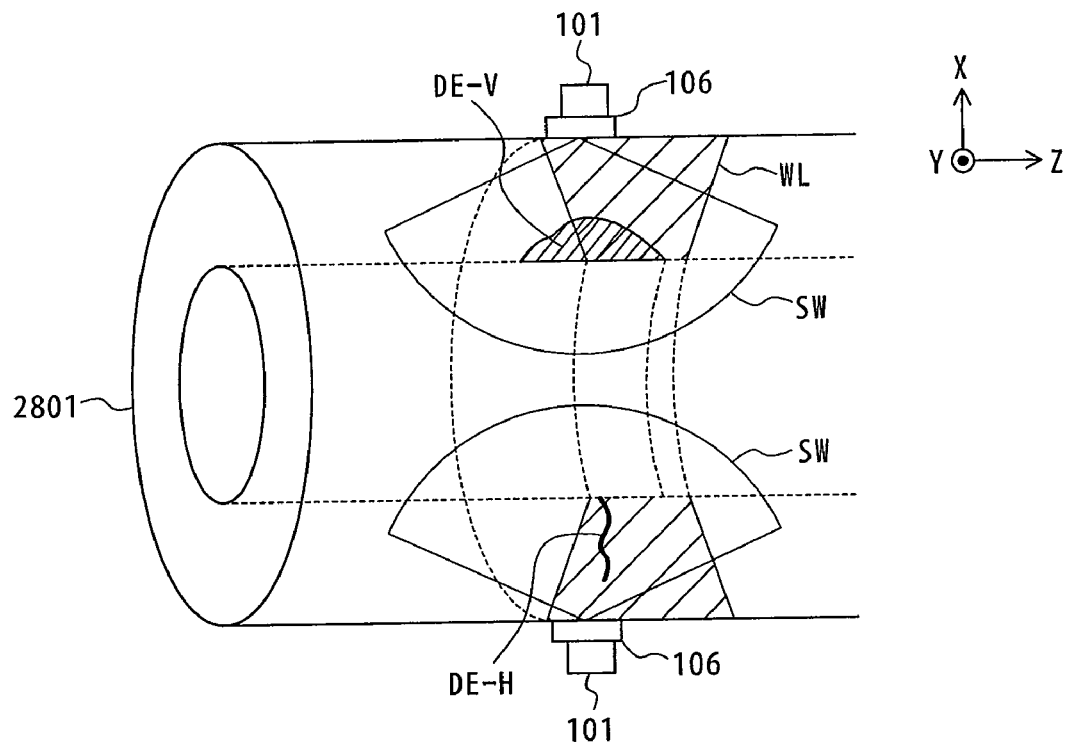
FIGS. 30A and 30B are explanatory diagrams each showing the positional relationship between a weld line and the probe (used in the ultrasonic inspection apparatus according to the embodiment of the present invention) placed on an outer surface of a tube, and the direction of propagation of the ultrasonic wave.
Figure 30B:
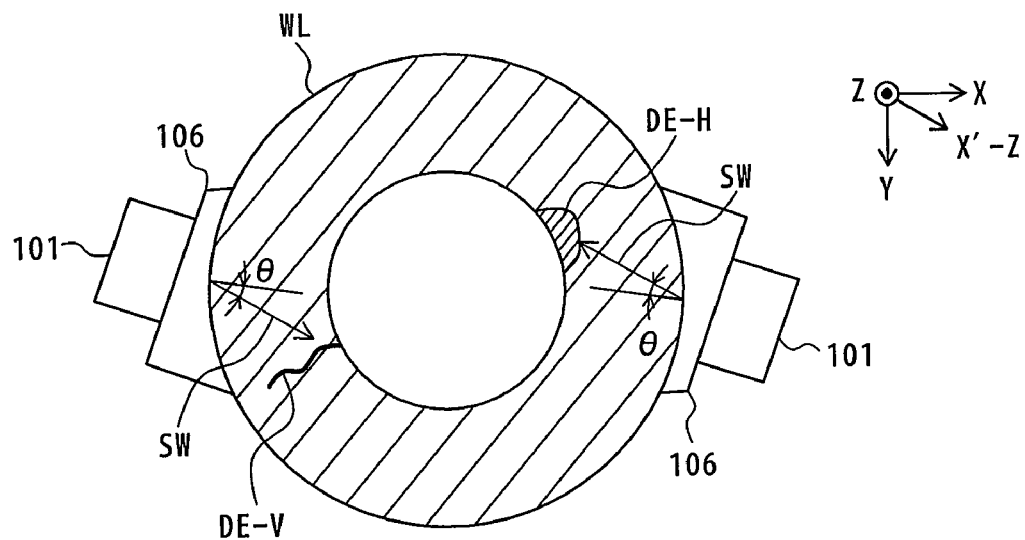

FIGS. 30A and 30B show the case where the weld line is inspected from the outer surface of a tube 2801. The tube 2801 has a weld line WL extending in the direction of a circumference of the tube 2801. It is assumed that the weld line 2801 has an axial crack defect DE-V or a circumferential crack defect DE-H on the side of the inner surface of the weld line WL. The ultrasonic wave SW is incident at an optional angle measured in the direction of an axis of the tube 2801 to scan the weld line WL as shown in FIG. 30A. In addition, the ultrasonic wave SW is incident at an angle θ with respect to a normal to the outer surface of the tube 2801 in an X'-Z plane defined by an X' axis and the Z axis to scan the weld line WL, where the X' axis is inclined at the angle θ with respect to the normal to the outer surface of the tube 2801. It is possible to detect a defect in the weld line WL and measure the size of the defect in the weld line WL, in the same manner as those for detecting a defect in each of the H8, H9 and H11 weld lines and measuring the length of the defect in each of the H8, H9 and H11 weld lines.

Figure 31A:
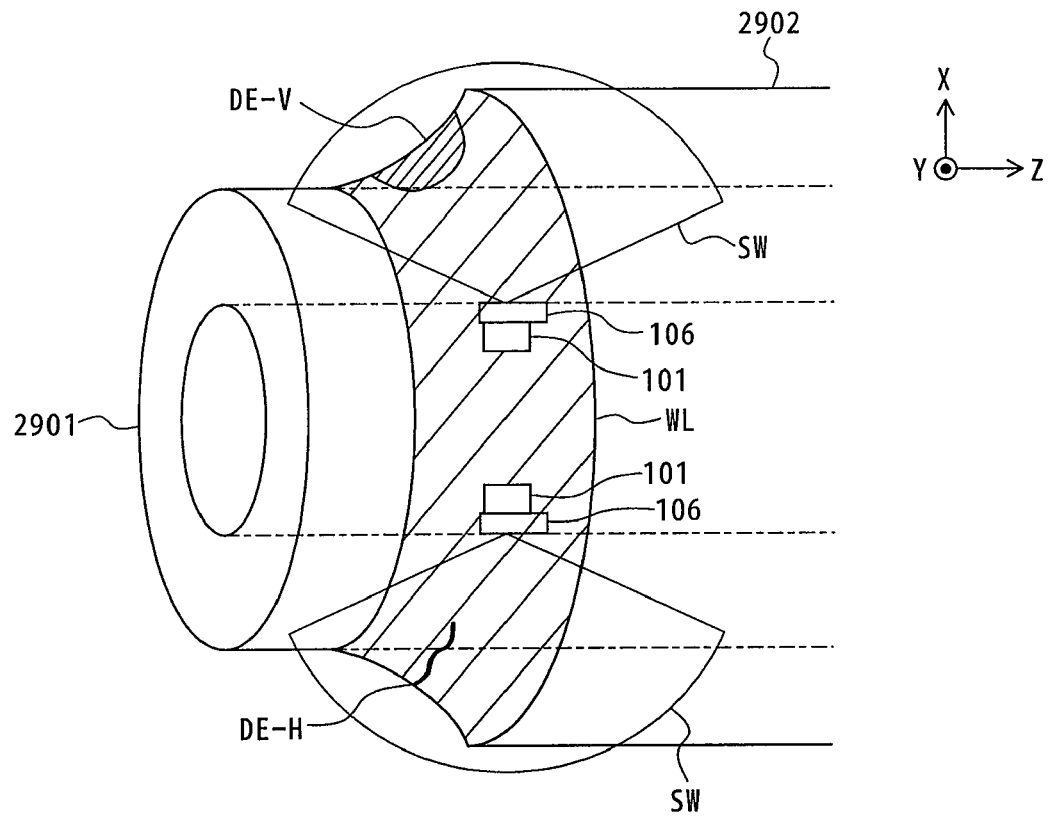
FIGS. 31A and 31B are explanatory diagrams each showing the positional relationship between a weld line and the probe (used in the ultrasonic inspection apparatus according to the embodiment of the present invention) placed on an inner surface of the tube, and the direction of propagation of the ultrasonic wave.
Figure 31B:
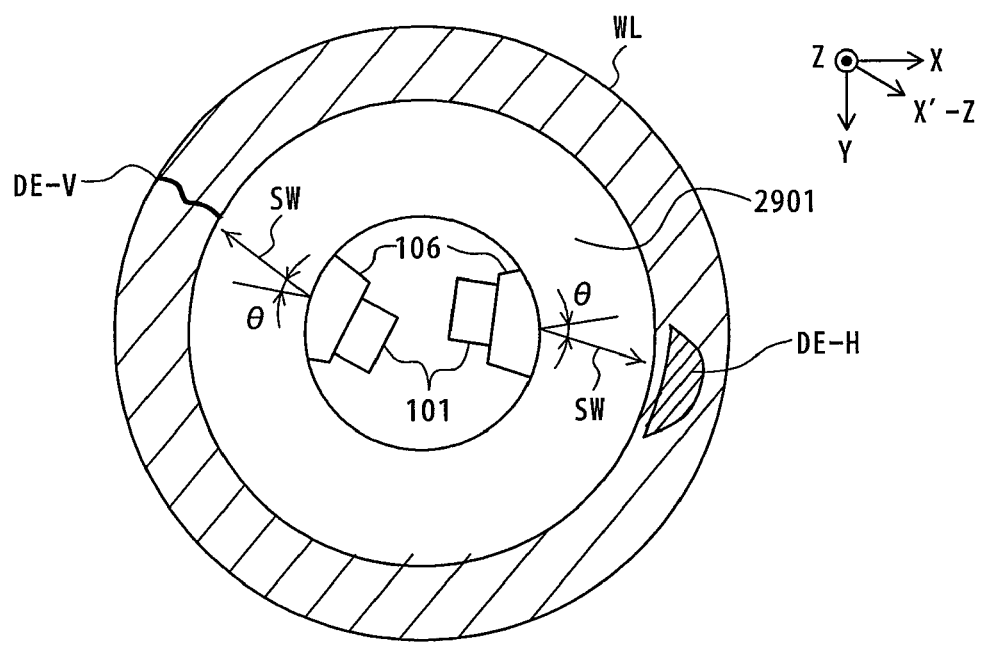

FIGS. 31A and 31B show the case where the weld line is inspected from the inner surface of a tube 2901. The tube 2901 and a tube 2902 are welded to each other by means of a circumferential weld line WL. It is assumed that the weld line WL has an axial crack DE-V or a circumferential crack DE-H on the side of the outer surface of the weld line WL. The ultrasonic wave SW is incident on the inner surface of the tube 2901 at an optional angle measured in the direction of an axis of the tube 2901 to scan the circumferential weld line WL as shown in FIG. 31A, and incident in an X'-Z plane defined by an X' axis and the Z axis, where the X' axis is inclined at an angle θ with respect to the normal to the inner surface of the tube 2901 as shown in FIG. 31B. It is possible to detect a defect in the circumferential weld line WL and measure the size of the defect in the circumferential weld line WL, in the same manner as those for detecting a defect in each of the H8, H9 and H11 weld lines and measuring the length of the defect in each of the H8, H9 and H11 weld lines.

The at least one ultrasonic probe is placed on the outer surface or inner surface of the tube and is thereby capable of detecting an axial crack and a circumferential crack in the welded part (extending in the circumferential direction of the tube) of the tube in a single operation.

In the example shown in FIGS. 30A to 31B, a single array probe is used to transmit and receive an ultrasonic wave. However, an array probe for transmitting an ultrasonic wave and another array probe for receiving an ultrasonic wave may be provided in the ultrasonic inspection apparatus according to the present embodiment.

According to the present embodiment, the ultrasonic probe is placed on a surface (that is to be scanned and located on the opposite side to a surface (of a structure (tube or vessel)) on which a welded part is present) of the structure to scan the welded part. The welded part joins the structure (partially or entirely having a cylindrical shape) and another structure in a circumferential direction or axial direction of the structure having the cylindrical shape. The ultrasonic probe placed in this way transmits an ultrasonic wave to detect an axial crack, a circumferential crack and the like, which are defects present in the welded part, in a single operation. This makes it possible to reduce the time for the inspection.

What is claimed is:

1. An ultrasonic inspection method comprising the steps of:
    placing an ultrasonic probe on a first surface of a first structure that is one of a tube and a vessel, which the first structure at least one of partially and entirely has a cylindrical shape, the first surface of the first structure being located on an opposite side to a second surface of the first structure on which the second surface of the first structure a welded part is present, the welded part joining the first structure and a second structure along at least one of a circumferential direction and an axial direction of the first structure having the cylindrical shape;
    transmitting an ultrasonic wave from the ultrasonic probe at an angle in an X'-Z plane defined by an X' axis and a Z axis, when the direction of a line that is normal to the first surface of the first structure is defined as an X axis, a direction in which the welded part extends is defined as a Y axis, a direction perpendicular to the X axis and the Y axis is defined as a Z axis, and an axis obtained by rotating the X axis around the Z axis is defined as an X' axis and wherein the X' axis is a single axis; and
    receiving a signal which is reflected from a defect present in the welded part to detect the presence of the defect.

2. The ultrasonic inspection method according to claim 1, further including:
    displaying the result of the inspection when the ultrasonic probe moves in at least one of the Y axis and the Z axis and transmits the ultrasonic wave at the angle in the X'-Z plane to inspect the welded part, the;
    specifying a target area is from the inspection result, and obtaining an accumulated value of at least one of the intensity of an echo generated in the specified target area and a variation of the intensity of the echo; and
    comparing at least one of the accumulated value and the variation obtained at a data acquisition point with the at least one of accumulated value and the variation obtained at another data acquisition point for detecting a defect.

3. The ultrasonic inspection method according to claim 1, further including:
measuring a length of the defect based on the signal reflected from the defect when the ultrasonic wave is transmitted at the angle to scan the welded part.

4. The ultrasonic inspection method according to claim 1, further including
overlapping data on an area in which an echo spreads and a cross sectional drawing showing the welded part to be inspected based on a position of a reflection source and displaying the resulting image and calculating, the position of the reflection source based on an beam path distance of an echo caused by the shape of the first structure and on an incident angle of the ultrasonic wave on the first surface of the first structure with respect to a normal to the first surface of the first structure.

5. An ultrasonic inspection apparatus comprising:
an ultrasonic probe usable to transmit an ultrasonic wave and to receive a signal reflected from a defect present in a welded part, the ultrasonic probe being positionable on a first surface of a first structure that is one of a tube and a vessel, which the first structure at least one of partially and entirely has a cylindrical shape, the first surface of the first structure being located on an opposite side to a second surface of the first structure on which the second surface of the first structure a welded part is present, the welded part joining the first structure and a second structure along at least one of a circumferential direction and an axial direction of the first structure having the cylindrical shape;
control means to control the ultrasonic wave transmitted by the ultrasonic probe to cause the ultrasonic wave to be transmitted at an angle;
ultrasonic wave direction changing means to change a direction of the transmission of the ultrasonic wave from a direction of an X axis to a direction of an X' axis to ensure that the ultrasonic wave is transmitted in the first structure by the ultrasonic probe in an X'-Z plane defined by the X' axis and a Z axis, when a direction of a line which is normal to the first surface of the first structure is defined as the X axis, a direction in which the welded part extends is defined as a Y axis, a direction perpendicular to the X axis and the Y axis is defined as the Z axis, and an axis obtained by rotating the X axis around the Z axis is defined as the X' axis; and
position changing means for moving the ultrasonic probe in at least one of a direction in which the welded part extends and in a direction which is perpendicular to the direction in which the welded part extends, wherein the defect present in the welded part is detected based on the signal reflected from the defect present in the welded part.

6. The ultrasonic inspection apparatus according to claim 5, wherein
the ultrasonic wave direction changing means is provided between the first surface of the first structure and the ultrasonic probe and is made of a medium in which the ultrasonic wave propagates at a speed different from that at which the ultrasonic wave propagates in the first structure.

7. The ultrasonic inspection apparatus according to claim 5, wherein
when the ultrasonic probe moves in at least one of the Y axis and the Z axis and transmits the ultrasonic wave at the angle in the X'-Z plane to inspect the welded part, the control means displays the result of the inspection (B scan), specifies a target area from the inspection result, obtains an accumulated value of the at least one of intensity of an echo generated in the target area and of a variation of the intensity of the echo, and compares the at least one of the accumulated value and the variation obtained at a data acquisition point with the at least one of the accumulated value and the variation obtained at another data acquisition point to detect the defect.

8. The ultrasonic inspection apparatus according to claim 5 further comprising a display and, in which display data on an area in which an echo spreads and a cross sectional drawing showing the welded part to be inspected are overlayed based on the position of a reflection source and a resulting image is displayed, the position of a reflection source being calculated based on a beam path distance of an echo caused by the shape of the first structure and on an incident angle of the ultrasonic wave on the first surface of the first structure with respect to a normal to the first surface of the first structure.

9. The ultrasonic inspection apparatus of claim 6 wherein said ultrasonic wave direction changing means is an acrylic shoe.

10. The ultrasonic inspection apparatus of claim 5, wherein said position changing means for moving the ultrasonic probe includes a rail secured to, and spaced from said first surface, said ultrasonic probe being movably positioned on said rail.

11. The ultrasonic inspection apparatus of claim 10 further including a case having spaced rollers, said rollers being in engagement with said rail and supporting said case for moving about said rail.

12. The ultrasonic inspection apparatus of claim 11, further including a base supported by said case and movable with respect to said base, said ultrasonic probe being attached to said base.

13. The ultrasonic inspection apparatus of claim 12, further including a column and a lead screw connecting said base to said case.

14. The ultrasonic inspection apparatus of claim 13 further including a drive motor able to rotate said lead screw to move said base along said column with respect to said base.

15. The ultrasonic inspection apparatus of claim 12, further including a gimbal mechanism connecting said ultrasonic probe to said base.

16. The ultrasonic inspection apparatus of claim 12, further including a pressing mechanism between said ultrasonic probe and said base.

17. The ultrasonic inspection method of claim 1, further including providing said angle in said X'-Z plane as being an oblique angle.

18. The ultrasonic inspection method of claim 17, further including providing said oblique angle being between 10° and 30°.

19. The ultrasonic inspection method of claim 1, further including providing a movable support for said ultrasonic probe and moving said ultrasonic probe during said transmitting and receiving of said ultrasonic wave.

* * * * *